(12) United States Patent
Carson et al.

(10) Patent No.: US 7,151,100 B1
(45) Date of Patent: *Dec. 19, 2006

(54) INDOLE COMPOUNDS USEFUL FOR THE TREATMENT OF CANCER

(75) Inventors: Dennis A. Carson, Del Mar, CA (US); Lorenzo M. Leoni, San Diego, CA (US); Howard B. Cottam, Escondido, CA (US)

(73) Assignee: The Regents of the University of California, Oakland, CA (US)

( * ) Notice: Subject to any disclaimer, the term of this patent is extended or adjusted under 35 U.S.C. 154(b) by 178 days.

This patent is subject to a terminal disclaimer.

(21) Appl. No.: 09/634,207

(22) Filed: Aug. 9, 2000

Related U.S. Application Data

(63) Continuation-in-part of application No. 09/360,020, filed on Jul. 23, 1999.

(60) Provisional application No. 60/189,976, filed on Mar. 16, 2000.

(51) Int. Cl.
| | |
|---|---|
| A61K 31/535 | (2006.01) |
| A61P 35/02 | (2006.01) |
| C07D 413/00 | (2006.01) |
| C07D 491/052 | (2006.01) |
| C01B 25/16 | (2006.01) |

(52) U.S. Cl. ............... 514/232.8; 514/81; 514/411; 544/142; 548/432; 423/316

(58) Field of Classification Search .......... 514/81, 514/232.8, 411; 544/142; 548/432; 423/316
See application file for complete search history.

(56) References Cited

U.S. PATENT DOCUMENTS

| | | |
|---|---|---|
| 3,053,255 A | 9/1962 | Meyer |
| 3,710,795 A | 1/1973 | Higuchi et al. |
| 3,843,480 A | 10/1974 | Dreher |

(Continued)

FOREIGN PATENT DOCUMENTS

| | | |
|---|---|---|
| CA | 1299577 | 4/1992 |
| DE | 2226 340 | 3/1973 |
| EP | 0289262 | 11/1986 |
| GB | 1436893 | 5/1976 |
| WO | 96/28148 | 9/1996 |
| WO | WO-9748391 A3 | 12/1997 |
| WO | 98/09603 | 3/1998 |
| WO | 98/18490 | 5/1998 |
| WO | WO-98/40078 A1 | 9/1998 |
| WO | 00/02555 | 1/2000 |
| WO | 00/13410 | 3/2000 |
| WO | WO-0106990 A2 | 2/2001 |
| WO | WO-02/021225 A1 | 1/2002 |
| WO | WO-0212188 A2 | 2/2002 |

OTHER PUBLICATIONS

Berendes, U.., et al. ,"Simultaneous Determination of the Phase II Metabolites of the Non Steriodal Anti–inflammatory Drug Etodolac in Human Urine", *Enantiomer*, vol. 1, (1996),415–422.

(Continued)

*Primary Examiner*—James O. Wilson
*Assistant Examiner*—Paul V. Ward
(74) *Attorney, Agent, or Firm*—Schwegman, Lundberg, Woessner & Kluth P.A.

(57) ABSTRACT

The present invention provides novel indole derivatives useful to inhibit cancer or sensitize cancer cells to chemotherapeutic agents, radiation or other anti-cancer treatments.

13 Claims, 15 Drawing Sheets

U.S. PATENT DOCUMENTS

| | | | |
|---|---|---|---|
| 3,843,681 A | 10/1974 | Demerson et al. | 260/326.14 R |
| 3,939,178 A | 2/1976 | Demerson et al. | |
| 3,948,254 A | 4/1976 | Zaffaroni | |
| 3,948,262 A | 4/1976 | Zaffaroni | |
| 3,974,179 A | 8/1976 | Demerson et al. | |
| 3,993,073 A | 11/1976 | Zaffaroni | |
| 4,041,169 A | 8/1977 | Demerson et al. | |
| 4,179,503 A | 12/1979 | Asselin et al. | |
| 4,310,509 A | 1/1982 | Berglund et al. | |
| 4,337,760 A | 7/1982 | Rubin | 128/1 R |
| 4,460,562 A | 7/1984 | Keith et al. | |
| 4,466,953 A | 8/1984 | Keith et al. | |
| 4,482,534 A | 11/1984 | Blank | |
| 4,485,097 A | 11/1984 | Bell | |
| 4,505,891 A | 3/1985 | Ito | |
| 4,533,540 A | 8/1985 | Blank | |
| 4,542,012 A | 8/1985 | Dell | |
| 4,542,013 A | 9/1985 | Keith et al. | |
| 4,560,555 A | 12/1985 | Snider | |
| 4,585,877 A | 4/1986 | Demerson et al. | |
| 4,597,961 A | 7/1986 | Etscorn | |
| 4,608,249 A | 8/1986 | Otsuka et al. | |
| 4,686,213 A | 8/1987 | Ferdinandi et al. | |
| 4,748,252 A | 5/1988 | Ferdinandi et al. | |
| 4,806,356 A | 2/1989 | Shaw | |
| 4,940,587 A | 7/1990 | Jenkins et al. | |
| 5,561,151 A | 10/1996 | Young et al. | 514/411 |
| 5,599,946 A | 2/1997 | Vincenzo et al. | |
| 5,776,967 A | 7/1998 | Kreft et al. | |
| 5,780,435 A | 7/1998 | Garnick et al. | |
| 5,811,558 A | 9/1998 | Adger et al. | 548/427 |
| 5,824,699 A | 10/1998 | Kreft et al. | |
| 5,955,504 A | 9/1999 | Wechter et al. | 514/568 |
| 5,968,974 A | 10/1999 | Kargman et al. | |
| 5,981,592 A | 11/1999 | Wechter et al. | |
| 6,066,741 A * | 5/2000 | Vigano et al. | 548/432 |
| 6,110,955 A | 8/2000 | Nudelman et al. | |
| 6,160,018 A | 12/2000 | Wechter et al. | |
| 6,300,313 B1 | 10/2001 | Engel et al. | |
| 6,545,034 B1 * | 4/2003 | Carson et al. | 514/411 |
| 6,552,055 B1 | 4/2003 | Spiegelman et al. | |
| 2002/0042375 A1 | 4/2002 | Heimbrook et al. | |
| 2003/0004143 A1 | 1/2003 | Prior et al. | |
| 2005/0239752 A1 | 10/2005 | Carson et al. | |

Brenna, E.., et al. ,"New Enzymatic and Chemical Approaches to Enantiopure Etodolac", *Tetrahedron*, 53, (1997),17769–17780.

Van Breemen, R..B. , et al. ,"Characterization of Oxygen–Linked Glucuronides by Laser Desorption Mass Spectrometry", *Biomed. Mass Spectrom.*, 11, Abstract Only, Chemical Abstracts, Abstract No. 101:106777c,(1984),278–283.

Venuti, M..C. ,et al. ,"Synthesis and Biological Evaluation of omega–(N,N,N–trialkylammonium)alkyl Esters and Thioesters of Carboxylic Acid Nonsteroidal Antiinflammatory Agents", *Pharm. Res.*, 6, Abstract Only, Chemical Abstracts, Abstract No. 112:111681y,(1989),867–873.

Abramson, S.B., et al., "The Mechanisms of Action of Nonsteroidal Antiinflammatory Drugs", *Arthritis & Rheumatism*, 32 (1), pp. 1–9, (Jan. 1989).

Alexanian, R., et al., "The Treatment of Multiple Myeloma", *The New England Journal of Medicine*, 330 (7), pp. 484–489, (Feb. 17, 1994).

Barlogie, B., et al., "Prognostic Factors with High–Dose Melphalan for Refractory Multiple Myeloma", *Blood*, 72 (6), pp. 2015–2019, (Dec. 1988).

Bataille, R., et al., "Multiple Myeloma", *New England Journal of Medicine*, 336 (23), pp. 1657–1664, (Jun. 5, 1997).

Becker–Scharfenkamp, U., et al., "Evaluation of the Stereoselective Metabolism of the Chiral Analgesic Drug Etodolac by High–Performance Liquid Chromatography", *Journal of Chromatography*, 621 (2), pp. 199–207, (Nov. 24, 1993).

Bellosillo, B., et al., "Aspirin and Salicylate Induce Apoptosis and Activation of Caspases in B–Cell Chronic Lymphocytic Leukemia Cells", *Blood*, 92 (4), pp. 1406–1414, (Aug. 15, 1998).

Brocks, D.R., et al., "Etodolac Clinical Pharmacokinetics", *Clinical Pharmacokinetics*, 26 (4), pp. 259–274, (1994).

Carson, D.A., et al., "Oral Antilymphocyte Activity and Induction of Apoptosis by 2–chloro–2'–arabino–fluoro–2'–deoxyadenosine", *Proc. Natl. Acad. Sci. USA*, 89 (7), pp. 2970–2974, (Apr. 1992).

Chinetti, G., et al., "Activation of Proliferator–activated Receptors α and γ Induces Apoptosis of Human Monocyte–derived Macrophages", *The Journal of Biological Chemistry*, 273 (40), pp. 25573–25580, (Oct. 2, 1998).

Cunningham, D., et al., "High–dose Melphalan for Multiple Myeloma: Long–term Follow–up Data", *Journal of Clinical Oncology*, 12 (4), pp. 764–768, (Apr. 1994).

Demerson, C.A., et al., "Etodolic Acid and Related Compounds. Chemistry and Antiinflammatory Actions of Some Potent Di– and Trisubstituted 1,3,4,9–Tetrahydropyrano[3,4–b] indole–1–acetic Acids", *Journal of Medicinal Chemistry*, 19 (3), pp. 391–395, (1976).

Demerson, C.A., et al., "Resolution of Etodolac and Antiinflammatory and Prostaglandin Synthetase Inhibiting Properties of the Enantiomers", *J. Med. Chem.*, 26 (12), pp. 1778–1780, (Dec. 1983).

Drachenberg, D.F., et al., "Treatment of Prostate Cancer: Watchful Waiting, Radical Prostatectomy, and Cryoablation", *Seminars in Surgical Oncology*, 18 (1), pp. 37–44, (Jan./Feb. 2000).

Duffy, C.P., et al., "Treatment of Prostate Cancer: Watchful Waiting, Radical Prostatectomy, and Cryoablation", *Seminars in Surgical Oncology*, 18 (1), pp. 37–44, Jan./Feb. 2000).

Hahnfeld, L.E., et al., "Prostate Cancer", *The Medical Clinics of North America—The Aging Male Patient*, 83 (5), pp. 1231–1245, (Sep. 1999).

Harousseau, J.L., et al., "Double–Intensive Therapy in High– Risk Multiple Myeloma", *Blood*, 79 (11), pp. 2827–2833, (Jun. 1, 1992).

Krajewski, S., et al., "Detection of Multiple Antigens on Western Blots", *Analytical Biochemistry*, 236 (2), Article No. 0160, pp. 221–228, (May 1996).

Landis, S.H., et al., "Cancer Statistics, 1998", *CA Cancer J. Clin.*, 48 (1), pp. 6–29, (1998).

Lee, D.H., et al., "Proteasome Inhibitors: Valuable New Tools For Cell Biologists", *Trends in Cell Biology*, 8, pp. 397–403, (1998).

Lehmann, J.M., et al., "Peroxisome Proliferator–activated Receptors α and γ Are Activated by Indomethacin and Other Non–steroidal Anti–inflammatory Drugs", *The Journal of Biological Chemistry*, 272 (6), pp. 3406–3410, (Feb. 7, 1997).

Leoni, L.M., et al., "Induction of an Apoptotic Program in Cell–Free Extracts by 2–Chloro–2'–deoxyadenosine 5'–Triphosphate and Cytochrome C", *PNAS, USA*, 95 (16), pp. 9567–9571, (Aug. 4, 1998).

Lochmüller, C.H., et al., "Chromatographic Resolution of Enantiomers—Selective Review", *Journal of Chromatography, 113 (3)*, pp. 283–302, (Oct. 22, 1975).

Martel, R.R., et al., "Anti–inflammatory and Analgesic Properties of Etodolic Acid in Rats", *Canadian Journal of Physiology and Pharmacology, 54 (3)*, pp. 245–248, (Jun. 1976).

Mooney, P.T., et al., "Cell Pathways' Exisulind 'Aptosyn' Demonstrates Potential to Delay Hormone Therapy in Post–Prostatectomy Men at Risk of Prostate Cancer Recurrence", http://biz.yahoo.com/bw/000501/ga_cell_pa_1.html, 3 p., (May 2000).

Ricote, M., et al., "The Peroxisome Proliferator–Activated Receptor–γ is a Negative Regulator of Macrophage Activation", *Nature, 391*, pp. 79–82, (Jan. 1, 1998).

Riedel, D.A., et al., "The Epidemiology of Multiple Myeloma", *Hematology/Oncology Clinics of North America, Multiple Myeloma, 6 (2)*, pp. 225–247, (Apr. 1992).

Royall, J.A., et al., "Evaluation of 2', 7'–Dichlorofluorescin and Dihydrorhodamine 123 as Fluorescent Probes for Intracellular $H_2O_2$ in Cultured Endothelial Cells", *Archives of Biochemistry and Biophysics, 302 (2)*, pp. 348–355, (May 1, 1993).

Shiff, S.J., et al., "Nonsteroidal Antiinflammatory Drugs Inhibit the Proliferation of Colon Adenocarcinoma Cells: Effects on Cell Cycle and Apoptosis", *Experimental Cell Research, 222*, Article No. 0023, pp. 179–188, (1996).

Tang, D.G., et al., "Target to Apoptosis: A Hopeful Weapon for Prostate Cancer", *The Prostate*, pp. 284–293, (1997).

Wang, X., et al., "Antipoptotic Action of 1,25–Dihydroxyvitamin $D_3$ Is Associated with Increased Mitochondrial MCL–1 and RAF–1 Proteins and Reduced Release of Cytochrome c", *Experimental Cell Research, 235 (1)*, Article No. EX973667, pp. 210–217, (1997).

Wechter, W.J., et al., "E–7869 (R–Flurbiprofen) Inhibits Progression of Prostate Cancer in the TRAMP Mouse", *Cancer Research, 60*, pp. 2203–2208, (Apr. 15, 2000).

Weiss, H.A., et al., "Aspirin, Non–Steroidal Anti–Inflammatory Drugs and Protection from Colorectal Cancer: a Review of the Epidemiological Evidence", *Scandinavian Journal of Gastroenterology, 31 (Suppl. 220)*, pp. 137–141, (1996).

Wilen, S.H., et al., "Strategies In Optical Resolutions", *Tetrahedron, 33 (21)*, Tetrahedron Report No. 38, pp. 2725–2736, (1977).

*Drug Facts and Comparisons, 1995 Edition*, Wolters Kluwer Co.,(1995),2775–2789.

Kolluri, S. K., et al., "The R–Enantiomer of the Nonsteroidal Antiinflammatory Drug Etodalac Binds Retinoid X Receptor and Induces Tumor–Selective Apoptosis", *Proc. Natl. Acad. Sci. USA, 102(7)*,(2005), 2525–2530.

Mycek, M. J., et al., "Anticancer Drugs", *Lippincott's Illustrated Reviews: Pharmacology, Second Edition*,(1997),373; 387–395.

Heath, Clark W., "Nonsteroidal Antiinflammatory Drugs and Human Cancer", *American Cancer Society, vol. 74, No. 10*,(Nov. 15, 1994),2885–2886.

McCracken, John D., "Antiproliferative Effects of the Enantiomers of Flurbiprofen", *Journal of Clinical Pharmacology*, (1996),540–545.

Piazza, Gary A., "Apoptois Primarily Accounts for the Growth–inhibitory Properties of Sulindac Metabolites and Involves a Mechanism That is Independent of Cyclooxygebase Inhibition, Cell Cycles Arrest, and p53 Induction", *Cancer Research, vol. 57*,(Jun. 15, 1997),2452–2459.

Riley, et al., "New Drugs: a six month review", *US Pharamacist, vol. 16*,(Sep. 1991),35–64.

Thun, Michael J., "Aspirin, NSAID's, and digestive tract cancers", *Cancer and Metastasis Reviews 13, Kluwer Academic Publishers.*, (1994),269–277.

Wechter, William J., "R–Flurbiprofen (E–7869), a chemopreventive and treatment of cancer", *Inflammopharmacology, vol. 8, No. 2*, (2000),189–206.

Wechter, William J., "R–Flurbiprofen Chemoprevention and Treatment of Intestinal Adememas in the APC min/+ Mouse Model: Implications for Prophylaxis and Treatment of Colon Cancer", *Cancer Research, vol. 57, No. 19*,(Oct. 1, 1997),4316–4324.

Wechter, William J., "Rac–Flubiprofen Is More Ulcerogenic Than Its (S)–Enatiomer", *Chirality, vol. 5, Number 7*,(1993), 492–494.

\* cited by examiner

INDOLE COMPOUNDS USEFUL FOR THE TREATMENT OF CANCER

CROSS-REFERENCE TO RELATED APPLICATIONS

This application is a continuation-in-part of U.S. patent application Ser. No. 09/360,020 filed Jul. 23, 1999, and claims priority of U.S. provisional patent application Serial No. 60/189,976, filed Mar. 16, 2000, both of which are incorporated by reference herein.

BACKGROUND OF THE INVENTION

The invention was made with Government support under Grant No. 5ROI GM23200-24 awarded by the National Institute of Health. The Government has certain rights in the invention.

Prostate cancer is the second leading cause of cancer death among males in the United States. In 1998, an estimated 185,000 men were diagnosed with prostate cancer, and more than 39,000 men died of the disease. See, S. H. Landis et al., Cancer Statistics, *CA Cancer J. Clin.,* 48, 6(1998). Although survival rates are good for prostate cancer that is diagnosed early, the treatments for advanced disease are limited to hormone ablation techniques and palliative care. Hormone ablation techniques (orchiectomy and anti-androgen treatments) generally allow only temporary remission of the disease. It usually recurs within 1–3 years of treatment, with the recurrent tumors no longer requiring androgens for growth and survival. D. G. Tang, et al., *Prostate,* 32, 284 (1997). Therapy with conventional chemotherapeutic agents, such as progesterone, estramustine and vinblastine, has also not been demonstrated to be effective to halt progression of the disease.

The number of nonsteroidal anti-inflammatory drugs (NSAIDs) has increased to the point where they warrant separate classification. In addition to aspirin, the NSAIDs available in the U.S. include meclofenamate sodium, oxyphenbutazone, phenylbutazone, indomethacin, piroxicam, sulindac and tolmetin for the treatment of arthritis; mefenamic acid and zomepirac for analgesia; and ibuprofen, fenoprofen and naproxen for both analgesia and arthritis. Ibuprofen, mefenamic acid and naproxen are used also for the management of dysmenorrhea.

The clinical usefulness of NSAIDs is restricted by a number of adverse effects. Phenylbutazone has been implicated in hepatic necrosis and granulomatous hepatitis; and sulindac, indomethacin, ibuprofen and naproxen with hepatitis and cholestatic hepatitis. Transient increases in serum aminotransferases, especially alanine aminotransferase, have been reported. All of these drugs, including aspirin, inhibit cyclooxygenase, that in turn inhibits synthesis of prostaglandins, which help regulate glomerular filtration and renal sodium and water excretion. Thus, the NSAIDs can cause fluid retention and decrease sodium excretion, followed by hyperkalemia, oliguria and anuria. Moreover, all of these drugs can cause peptic ulceration. See, *Remington's Pharmaceutical Sciences,* Mack Pub. Co., Easton, Pa. (18th ed., 1990) at pages 1115–1122.

There is a large amount of literature on the effect of NSAIDs on cancer, particularly colon cancer. For example, see H. A. Weiss et al., *Scand J. Gastroent.,* 31, 137 (1996) (suppl. 220) and Shiff et al., *Exp. Cell Res.,* 222, 179 (1996). More recently, B. Bellosillo et al., *Blood,* 92, 1406 (1998) reported that aspirin and salicylate reduced the viability of B-cell CLL cells in vitro, but that indomethacin, ketoralac and NS-398, did not.

C. P. Duffy et al., *Eur. J. Cancer,* 34, 1250 (1998), reported that the cytotoxicity of certain chemotherapeutic drugs was enhanced when they were combined with certain nonsteroidal anti-inflammatory agents. The effects observed against human lung cancer cells and human leukemia cells were highly specific and not predictable; i.e., some combinations of NSAID and agent were effective and some were not. The only conclusion drawn was that the effect was not due to the cyclooxygenase inhibitory activity of the NSAID.

The Duffy group filed a PCT application (WO98/18490) on Oct. 24, 1997, directed to a combination of a "substrate for MRP", which can be an anti-cancer drug, and a NSAID that increases the potency of the anti-cancer drug. NSAIDs recited by the claims are acemetacin, indomethacin, sulindac, sulindac sulfide, sulindac sulfone, tolmetin and zomepirac. Naproxen and piroxicam were reported to be inactive.

Recently, W. J. Wechter et al., *Cancer Res.,* 60, 2203 (2000) reported that the NSAID, R-flurbiprofen, inhibited progression of prostate cancer in the TRAMP mouse, a prostate cancer model. The Wechter group filed a PCT application (WO98/09603) on Sep. 8, 1997, disclosing that prostate cancer can be treated with R-NSAIDs, including R(−)-etodolac and R-flurbiprofen. In contrast to R(−)-etodolac, the R-enantiomer of flurbiprofen and other (R)-2-aryl propionate NSAIDs are converted in the body to the anti-inflammatory S-enantiomers, and hence are pro-drugs of the NSAIDs, while R(−) etodolac is not per se an NSAID. Therefore, a continuing need exists for effective methods to employ these preliminary findings to develop new compounds to treat neoplastic disease, including prostate cancer and other cancers.

SUMMARY OF THE INVENTION

The present invention provides indole compounds of formula (I):

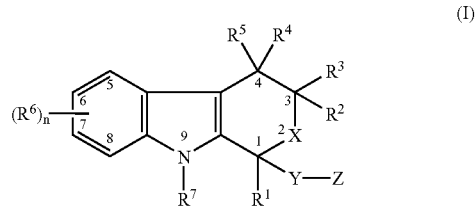

wherein $R^1$ is lower alkyl, lower alkenyl, (hydroxy)lower alkyl, lower alkynyl, phenyl, benzyl or 2-thienyl, $R^2$, $R^3$, $R^4$ and $R^5$ are the same or different and are each hydrogen or lower alkyl; each $R^6$ is individually hydrogen, lower alkyl, hydroxy, (hydroxy)lower alkyl, lower alkoxy, benzyloxy, lower alkanoyloxy, nitro or halo, n is 1–3, $R^7$ is hydrogen, lower alkyl or lower alkenyl, X is oxy and thio, Y is carbonyl, $(CH_2)_{1-3}$, $(CH_2)_{1-3}C(O)$, or $(CH_2)_{1-3}SO_2$ and Z is (ω-(4-pyridyl)($C_2$–$C_4$ alkoxy), (ω-(($R^8$)($R^9$) amino) ($C_2$–$C_4$ alkoxy), wherein $R^8$ and $R^9$ are each H, ($C_1$–$C_3$)alkyl or together with N are a 5- or 6-membered heterocyclic ring comprising 1–3 $N(R^8)$, S or nonperoxide O; an amino acid ester of (ω-(HO)($C_2$–$C_4$))alkoxy, $N(R^8)CH(R^8)CO_2H$, 1'-D-glucuronyloxy, OH, ($C_2$–$C_4$)acyloxy, $SO_3H$, $PO_4H_2$, N(NO)(OH), $SO_2NH_2$, $PO(OH)NH_2$, $OCH_2CH_2N(CH_3)_3^+$ or tetrazolyl; or a pharmaceutically acceptable salt thereof.

The present invention also provides a therapeutic method to inhibit the growth of cancer calls and/or to sensitize cancer cells to inhibition by a chemotherapeutic agent. The method comprises contacting cancer cells with an effective amount of the compound of formula (I), preferably in combination with a pharmaceutically acceptable carrier. The present compounds can be used to treat a mammal afflicted with cancer, such as a human cancer patient, and are preferably administered in conjunction with a chemotherapeutic agent, such as an alkylating agent or an antiandrogen, radiation and/or other anti-cancer therapy.

The present compounds are effective against hematopoietic cancers, such as leukemias and cancers of the bone marrow, including chromic lymphocytic leukemia (CLL) and multiple myeloma (MM). The present compounds were unexpectedly found to be effective against cancer cells that express high levels of the nuclear hormone receptor, peroxisome proliferator activated receptor-γ, (PPAR-γ), and/or high levels of the anti-apoptotic proteins, Mcl-1 and/or Bag-1. Such cancer cells include at least some types of prostate cancer cells.

Activated PPAR-γ binds co-activator protein (CBP), a co-activator of the androgen receptor known to be overexpressed in hormone-resistant prostate cancer. Thus, compounds of formula (I) that activate PPAR-γ production can reduce the level of expression of the androgen receptor known to be over-expressed in hormone-resistant prostate cancer. Therefore, the present compounds can enhance the efficacy of conventional anti-androgen therapy, and can act to inhibit the spread of prostate cancer.

The present invention is based on the discovery by the inventors that racemic etodolac inhibits the viability of purified CLL or MM cells at concentrations that do not inhibit the viability of normal peripheral blood lymphocytes (PBLs). It was then unexpectedly found that the R(−) enantiomer of etodolac is as toxic to CLL cells as is the S(+) enantiomer. It was then found that etodolac synergistically interacted with fludarabine and 2-chlorodenosine to kill CLL cells at concentration at which the chemoteraputic agents alone were inactive. Finally, it was found that both R(−)- and S(+)-etodolac inhibited a number of prostate cancer cell lines. Again the R(−) enantiomer was at least as effective as the S(+)-"anti-inflammatory" enantiomer. This was unexpected since the R(−) enantiomer of etodolac does not possess significant anti-inflammatory activity and is not converted to the S(+) enantiomer to a significant extent in vivo. As noted above, the R-enantiomers of other R-2-arylpropionate NSAIDs are converted to the "active" anti-inflammatory S-enantiomers in vivo, and so function as pro-drugs for the NSAID.

The extent of inhibition was markedly related to the level of expression of PPAR-γ by the cell line. Cell lines with an elevated level of PPAR-γ expression were inhibited much more effectively than cell lines expressing relatively low levels of PPAR-γ, as disclosed in the working examples.

A compound of formula (I) is preferred for practice of the present therapeutic method that does not exhibit undesirable bioactivities due to inhibition of cyclooxygenase (COX) that are exhibited by some NSAIDs. However, the preferred compounds of formula (I) would not be considered NSAIDs by the art, as they would not exhibit significant anti-inflammatory activity.

Thus, the present invention also provides a method for determining whether or not a particular cancer patient, such as a prostate cancer patient, is amenable to treatment by a compound of formula (I), comprising isolating cancer cells and evaluating in vitro the relative level of PPAR-γ and/or Mcl-1 and/or Bag-1 relative to the level in a cancer cell line, such as prostate cancer line, known to be susceptible to treatment by a compound of formula (I).

The present invention also provides a method to determine the ability of a test agent to inhibit cancer cells, such as prostate cancer cells, comprising contacting a population of cancer cells, as from a prostate cancer cell line, with said agent and determining whether the agent increases expression of PPAR-γ, or decreases the expression of Mcl-1 and/or Bag-1 (or does both). The present invention also provides a general multilevel screening method to evaluate etodolac analogs, other NSAIDs or other agents for their ability to inhibit cancer, preferably etodolac-sensitive cancers, such as prostate cancer, CLL and MM. Agents that exhibit a positive activity, preferably at least equal to that of R(−)-etodolac, or do not exhibit a negative activity, e.g., are no more active than R(−)-etodolac, are passed to the next screen.

Test agents are first evaluated for their ability to competitively inhibit the binding of etodolac, e.g., radiolabeled R(−) etodolac to its receptor(s) on etodolac-sensitive cancer cells such as CLL cells. Agents that can compete effectively with R(−) etodolac for etodolac binding site(s) on the cells are then evaluated in an assay to determine if they can increase $Ca^{+2}$ uptake in cancer cells, such as CLL cells, preferably as effectively as R(−) etodolac. Agents that can induce intracellular $Ca^{+2}$ uptake are screened to determine if they can induce chemokinetic activity (chemokinesis or chemotaxis) in a population of lymphocytes, such as B-CLL lymphocytes, preferably as effectively as R(−) etodolac. Agents that are positive in this screen are then evaluated to determine if they can induce apoptosis or pro-apoptotic factors, such as increased caspase activity in cancer cells, such as CLL cells and other cancer cells known to be etodolac sensitive, at least as effectively as R(−) etodolac.

Agents that test positive in this screen are evaluated for their ability to deplete lymphocytes in mice, and those that are no more active than R(−) etodolac are then evaluated in animal models of cancer to see if they can inhibit the induction of, or spread of cancer.

As used herein with respect to cancer or cancer cells, the term "inhibition" or "inhibit" includes both the reduction in cellular proliferation, blockage of cellular proliferation, or killing some or all of said cells. Thus, the term can be used in both the context of a prophylactic treatment to prevent development of cancer or as a treatment that will block, or slow the spread of established cancer. Whether or not the level of expression of a marker of susceptibility to etodolac treatment is sufficiently elevated to continue treatment with etodolac or an analog thereof is determined by comparison between the relative levels of expression of said marker in resistant and susceptible cancer cell lines, as disclosed hereinbelow.

DETAILED DESCRIPTION OF THE INVENTION

Figure 1:
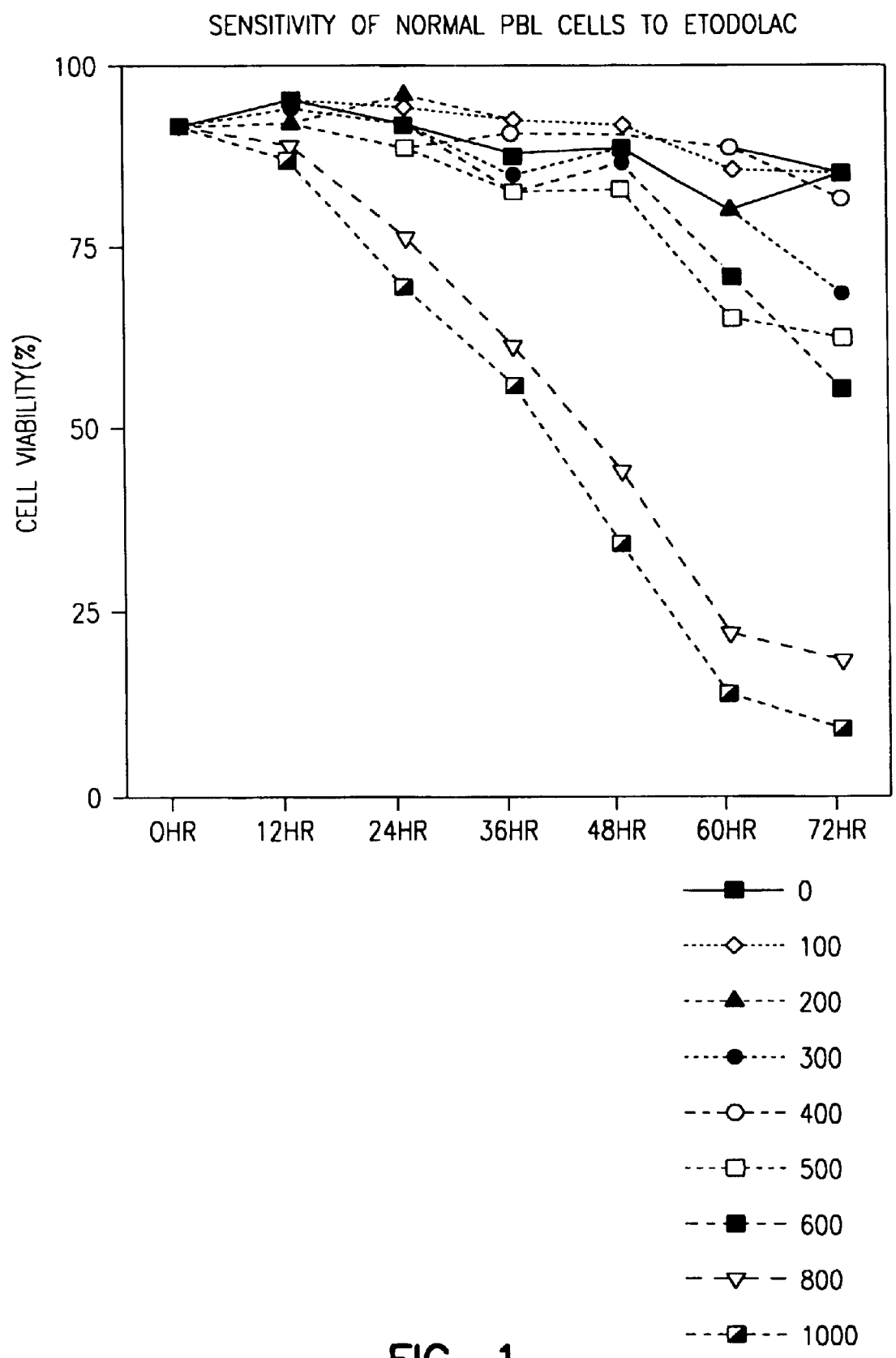
FIG. 1 is a graph depicting the sensitivity of normal peripheral blood lymphocytes (PBL) to racemic etodolac.

Indole compounds of the present inventions include compounds of formula (I):

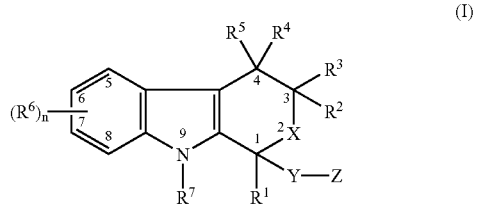

wherein $R^1$ is selected from the group consisting of lower alkyl, lower alkenyl, (hydroxy)lower alkyl, lower alkynyl, phenyl, benzyl and 2-thienyl, $R^2$, $R^3$, $R^4$ and $R^5$ are the same or different and are each selected from the group consisting of hydrogen and lower alkyl, each $R^6$ is individually selected from the group consisting of hydrogen, lower alkyl, hydroxy, (hydroxy)lower alkyl, lower alkoxy, benzyloxy, lower alkanoyloxy, nitro and halo, n is 1–3, $R^7$ is selected from the group consisting of hydrogen, lower alkyl and lower alkenyl, X is selected from the group consisting of oxy and thio, Y is selected from the group consisting of carbonyl $(CH_2)_{1-3}$, $(CH_2)_{1-3}SO_2$ or $(CH_2)_{1-3}C(O)$, and Z is selected from the group consisting of hydroxy, lower alkoxy optionally substituted with OH, 4-pyridyl, amino, lower alkylamino, di(lower alkyl)amino, or N-morpholino; amino, lower alkylamino, amino, di(lower)alkylamino and phenylamino, OH, $(C_2–C_4)$acyloxy, $SO_3H$, $PO_4H_2$, N(NO)(OH), $SO_2NH_2$, $PO(OH)NH_2$, $OCH_2CH_2N(CH_3)_3^+$ or tetrazolyl or a pharmaceutically acceptable salt thereof. Lower alkyl, alkenyl, alkanoyl, etc. indicates a branched, cyclic or straight chain $C_1–C_6$ group, preferably a $C_1–C_4$ group, including cycloalkyl and (cycloalkyl)alkyl. (Hydroxy)lower alkyl or alkoxy is preferably 1- or 2-hydroxyethyl.

As discussed above, the relatively low water solubility of the R(−) enantiomer of etodolac can reduce its usefulness against cancer when administered orally, or in an aqueous vehicle. Therefore, the present invention also provides novel indole compounds that exhibit enhanced water solubility and/or bioavailability over the free acid or the simple alkyl esters of etodolac. Such analogs include (pyridinyl) lower alkyl esters, (amino)lower alkyl esters, (hydroxy)lower alkyl esters and 1'-D-glucuronate esters of etodolac, e.g., compounds of formula (II) wherein (a) Y is carbonyl and (b) Z is (ω-(4-pyridyl)($C_2–C_4$ alkoxy), (ω-(($R^8$)($R^9$) amino)($C_2–C_4$ alkoxy), wherein $R^8$ and $R^9$ are each H, $(C_1–C_3)$ alkyl or together with N are a 5- or 6-membered heterocyclic ring comprising 1–3 $N(R^8)$, S or nonperoxide O; an amino acid ester of (ω-(HO)($C_2–C_4$)alkoxy, e.g., the L-valine or L-glycine ester of 2-hydroxyethoxy, 1'-D-glucuronyloxy; and the pharmaceutically acceptable salts thereof, e.g., with organic or inorganic acids. Other analogs of increased water solubility include amino acid amides, where Y is carbonyl and Z is $N(R^8)CH(R^8)CO_2H$, and the pharmaceutically acceptable salts thereof.

Such compounds can be prepared as disclosed in U.S. Pat. No. 3,843,681, U.S. patent application Ser. No. 09/313,048, Ger. Pat. No. 2,226,340 (Amer. Home Products), R. R. Martel et al., Can. J. Pharmacol., 54, 245 (1976); Demerson et al., J. Med. Chem., 19, 391 (1976); PCT application Serial No. US/00/13410 and Rubin (U.S. Pat. No. 4,337,760).

The resolution of racemic compounds of formula (I) can be accomplished using conventional means, such as the formation of a diastereomeric salt with a optically active resolving amine; see, for example, "Stereochemistry of Carbon Compounds," by E. L. Eliel (McGraw Hill, 1962); C. H. Lochmuller et al., J Chromatog., 113, 283 (1975); "Enantiomers, Racemates and Resolutions," by J. Jacques, A. Collet, and S. H. Wilen, (Wiley-Interscience, New York, 1981); and S. H. Wilen, A. Collet, and J. Jacques, Tetrahedron, 33, 2725 (1977). For example, the racemate has been resolved by fractional crystallization of RS-etodolac using optically active 1-phenylethylamine and HPLC has been used to determine racemic etodolac and enantiomeric ratios of etodolac and two hydroxylated metabolutes in urine (U. Becker-Scharfenkamp et al., J. Chromatog., 621, 199 (1993)). B. M. Adger et al. (U.S. Pat. No. 5,811,558), disclosed the resolution of etodolac using glutamine and N($C_1–C_4$ alkyl)-glutamine salts.

Etodolac itself (1,8-diethyl-1,3,4,9-tetrahydro[3,4-6] indole-1-acetic acid) is a NSAID of the pyranocarboxylic acid class, that was developed in the early 1970s. Its structure is depicted as formula (II), below, wherein (*) denotes the chiral center. See also, The Merck Index, (11th ed.), at page 608.

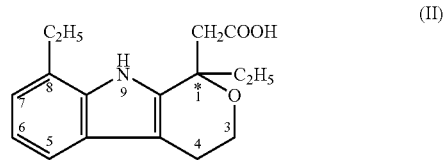

The pharmacokinetics of etodolac have been extensively reviewed by D. R. Brocks et al., Clin. Pharmacokinet., 26, 259 (1994). Etodolac is marketed as the racemate. The absolute configurations of the enantiomers were found to be S-(+) and R-(−), which is similar to that for most other NSAIDs. However, Demerson et al., J. Med. Chem., 26, 1778 (1983) found that the S(+)-enantiomer of etodolac possessed almost all of the anti-inflammatory activity of the racemate, as measured by reduction in paw volume of rats with adjuvant polyarthritis, and prostaglandin synthetase inhibitory activity of the drug. No anti-inflammatory activity was discernible with the (−)-enantiomer, and it is not converted significantly to the S(+) enantiomer in vivo. Hence, R(−) etodolac is not a NSAID. However, as disclosed below, R(−) etodolac paradoxically was found to have potent activity against cancer cells that is at least equivalent to that of the S(+) enantiomer.

Etodolac possesses several unique disposition features due to their stereoselective pharmacokinetics. In plasma, after the administration of RS-etodolac, the concentrations of the "inactive" R-enantiomer of etodolac are about 10-fold higher than those of the active S-enantiomer, an observation that is novel among the chiral NSAIDs. See, D. R. Brocks et al., *Clin. Pharmacokinet.*, 26, 259 (1994). After a 200 mg dose in six elderly patients, the maximum plasma concentration of the R-enantiomer was about 33 µM. In contrast, the maximum concentration of the S-enantiomer was 5-fold lower. The typical dosage of the racemic mixture of etodolac is 400 mg BID, and the drug has an elimination half-life between 6–8 hours. Moreover, it is likely that the administration of the purified R-enantiomer will not display the side effects associated with cyclooxygenase (COX) inhibitors, such as ulcers and renal insufficiency, and thus can be given at considerably higher dosages. Nonetheless, the relatively low solubility of R(–)-etodolac in water can impede attaining plasma levels in humans that can inhibit cancer cells, particularly prostate cancer cells. However, the compounds of formula (I) can be dissolved in water and other aqueous carriers at substantially higher concentrations than R(–) etodolac.

The compounds of formula (I) can also be prepared in the form of their pharmaceutically acceptable salts or their non-pharmaceutically acceptable salts. The non-pharmaceutically acceptable salts are useful as intermediates for the preparation of pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (b) salts formed from elemental anions such as chlorine, bromine, and iodine. Preferred carboxylic acid salts are those of hydrophilic amines, such as glucamine or N-($C_1$–$C_4$) alkylglucamine (see, Adger et al. (U.S. Pat. No. 5,811,558)).

The magnitude of a prophylactic or therapeutic dose of a compound or compounds of formula (I) in the acute or chronic management of cancer, i.e., prostate cancer, will vary with the type and/or stage of the cancer, the adjunct chemotherapeutic agent(s) or other anti-cancer therapy used, and the route of administration. The dose, and perhaps the dose frequency, will also vary according to the age, body weight, condition, and response to the individual patient. In general, the total daily dose range for a compound or compounds of formula (I), for the conditions described herein, is from about 50 mg to about 5000 mg, in single or divided doses. Preferably, a daily dose range should be about 100 mg to about 4000 mg, most preferably about 1000–3000 mg, in single or divided doses, e.g., 750 mg every 6 hr of orally administered compound. This can achieve plasma levels of about 500–750 µM, which can be effective to kill cancer cells. In managing the patient, the therapy should be initiated at a lower dose and increased depending on the patient's global response. It is further recommended that infants, children, patients over 65 years, and those with impaired renal or hepatic function initially receive lower doses, particularly of analogs which retain COX inhibitory activity, and that they be titrated based on global response and blood level. It may be necessary to use dosages outside these ranges in some cases. Further, it is noted that the clinician or treating physician will know how and when to interrupt, adjust or terminate therapy in conjunction with individual patient response. The terms "an effective inhibitory or amount" or "an effective sensitizing amount" are encompassed by the above-described dosage amounts and dose frequency schedule.

Any suitable route of administration may be employed for providing the patient with an effective dosage of a compound of formula (I). For example, oral, rectal, parenteral (subcutaneous, intravenous, intramuscular), intrathecal, transdermal, and like forms of administration may be employed. Dosage forms include tablets, troches, dispersions, suspensions, solutions, capsules, patches, and the like. The compound may be administered prior to, concurrently with, or after administration of chemotherapy, or continuously, i.e., in daily doses, during all or part of, a chemotherapy regimen. The compound, in some cases, may be combined with the same carrier or vehicle used to deliver the anti-cancer chemotherapeutic agent.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrated agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to othewise modify the physical form of the solid unit dosage form. For instance, tablets, pills, or capsules may be coated with gelatin, wax, shellac or sugar and the like. Tablets, capsules, pills, granules, microparticles and the like can also comprise an enteric coating, such as a coating of one of the Eudragit® polymers, that will permit release of the active compound(s) in the intestines, not in the acidic environment of the stomach. This can be advantageous in the case of elderly or frail cancer patients treated with any compound that retains a significant COX-inhibitory activity, and concomitant ulceration.

A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a non-toxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, non-toxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the techniques, which yield a powder of the active ingredient plus any additional desired ingredient present in the previously sterile-filtered solutions.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Due to the ability of compounds of formula (I) that elevate PPAR-γ levels, to lower the expression of the androgen receptor known to be overexpressed in hormone-refractory prostate cancer, compounds that upregulate PPAR-γ are advantageously used in combination with steroidal and non-steroidal anti-androgens used in the treatment of prostate cancer. These compounds include leuprolide or goserelin acetate, bicalutamide and flutamide, nilutamide, cycloproterone acetate, among others.

Due to the ability of compounds of formula (I) that reduce PPAR-γ levels to sensitize prostate cancer cells to killing by conventional chemotherapeutic agents, such compounds can be employed with chemotherapeutic agents used to treat cancers such as prostate cancer, including estramustine, vinblastine, mitoxanthrone, prednisone and the like, or melphalan to treat MM. Other chemotherapeutic agents, irradiation or other anti-cancer agents such as anti-tumor antibodies, or cytokines can be used with the present compounds. See, e.g., *Remington's Pharmaceutical Sciences* (18th ed. 1990) at pages 1138–1162.

The invention will be further described by reference to the following detailed examples.

EXAMPLE 1

Sensitivity of Normal Peripheral Blood Lympocytes and CLL Cells to Etodolac

Mononuclear cells were isolated from the peripheral blood of B-CLL patients and normal donors using density gradient centrifugation (Ficoll-Paque). Cells were cultured at $2\times10^6$ cells per mL in RPMI with 20% autologous plasma in 96-well plates with or without the indicated μM concentrations of etodolac (racemic, S-etodolac, R-etodolac) and in combination with 2-chloro-2'-deoxyadenosine (2 CdA) or fludarabine. At indicated times (12, 24, 36, 48, 60, 72 hours), viability assays were performed using the erythrocin B exclusion assay, as described by D. Carson et al., *PNAS USA*, 89, 2970 (1992).

As shown in FIG. 1, significant death of normal PBLs occurred only at 800 μM racemic etodolac, a concentration which cannot be obtained in vivo.

Figure 2:
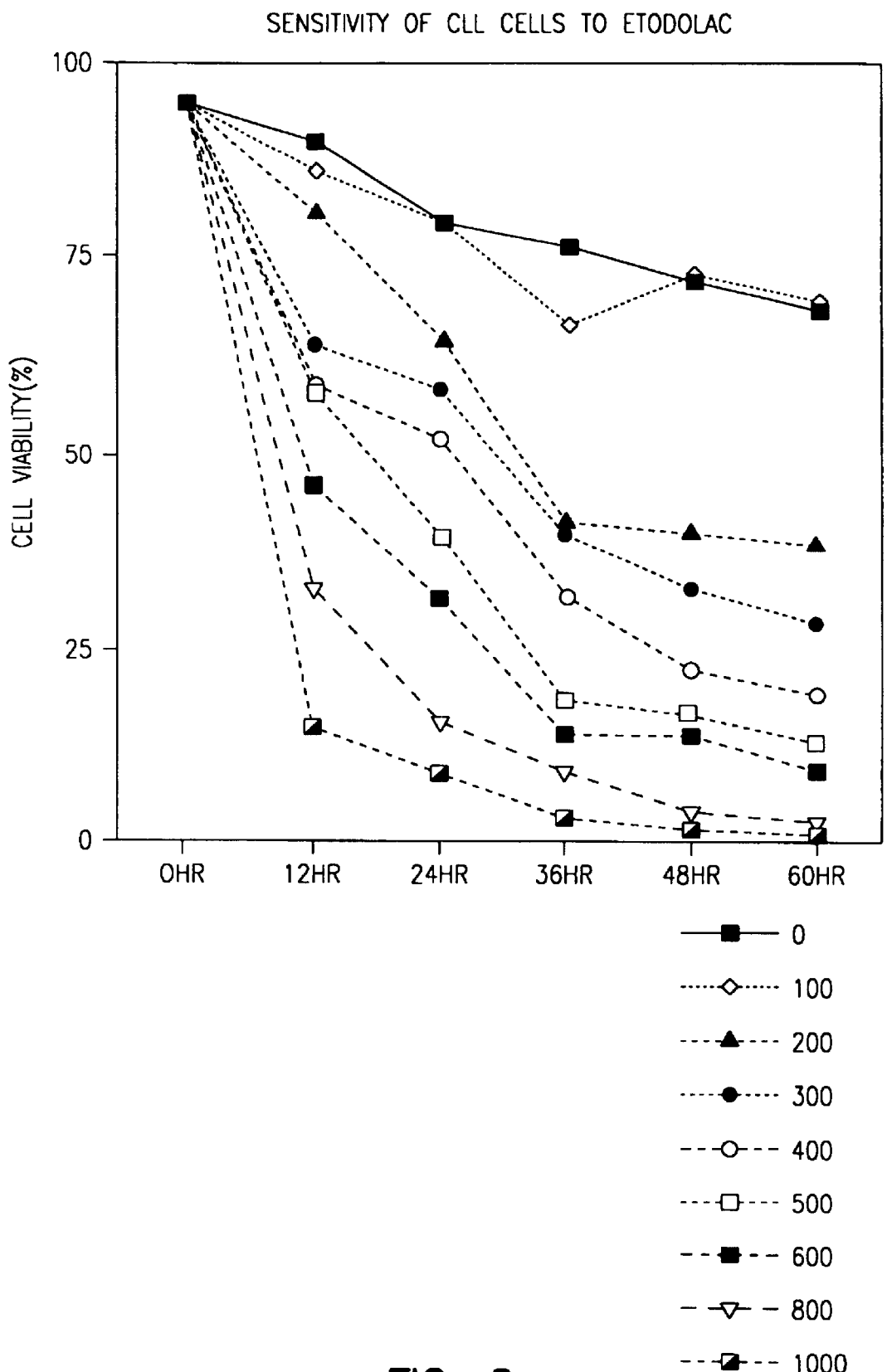
FIG. 2 is a graph depicting the sensitivity of CLL cells to racemic etodolac.

Peripheral blood lymphocytes from a normal donor were cultured with 1.0 mM etodolac for 24 hours. Then B lymphocytes were identified by staining with anti-CD19 antibody, and viability was assessed by $DiOC_6$ fluorescence. Etodolac under these conditions did not reduce the viability of the normal B cells, compared to control cultures. When the same viability assay was run with purified CLL cells from the peripheral blood of a CLL patient, the results were different. As shown in FIG. 2, 50% of the CLL cells were killed by a 48 hour exposure to 200 μM racemic etodolac. More than 95% of the treated cells were malignant B lymphocytes.

EXAMPLE 2

Synergistic Combinations of Etodolac and Chemotherapeutic Agents

Figure 3:
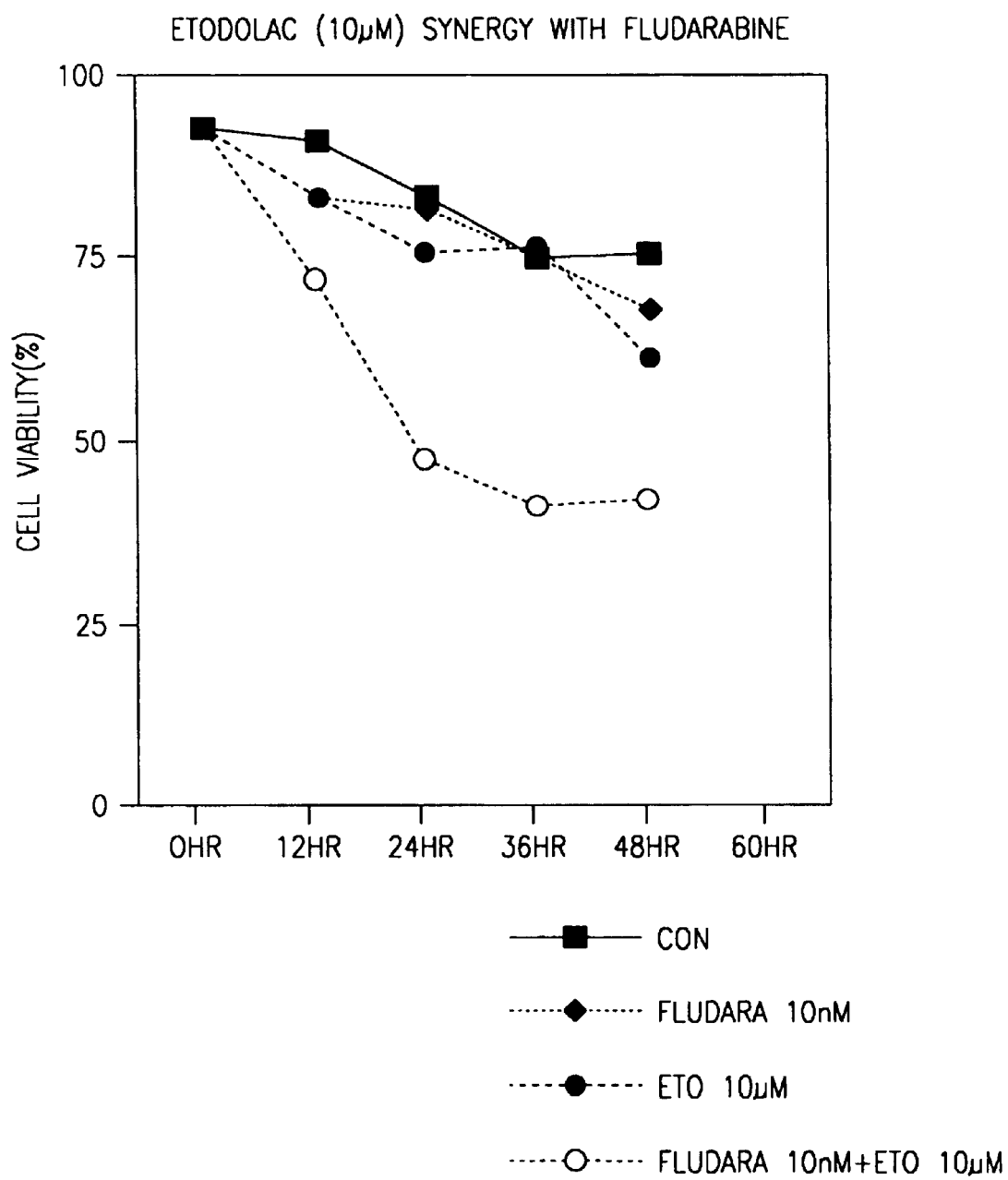
FIG. 3 is a graph depicting the synergistic effect of a combination of racemic etodolac and fludarabine against CLL cells.
Figure 4:
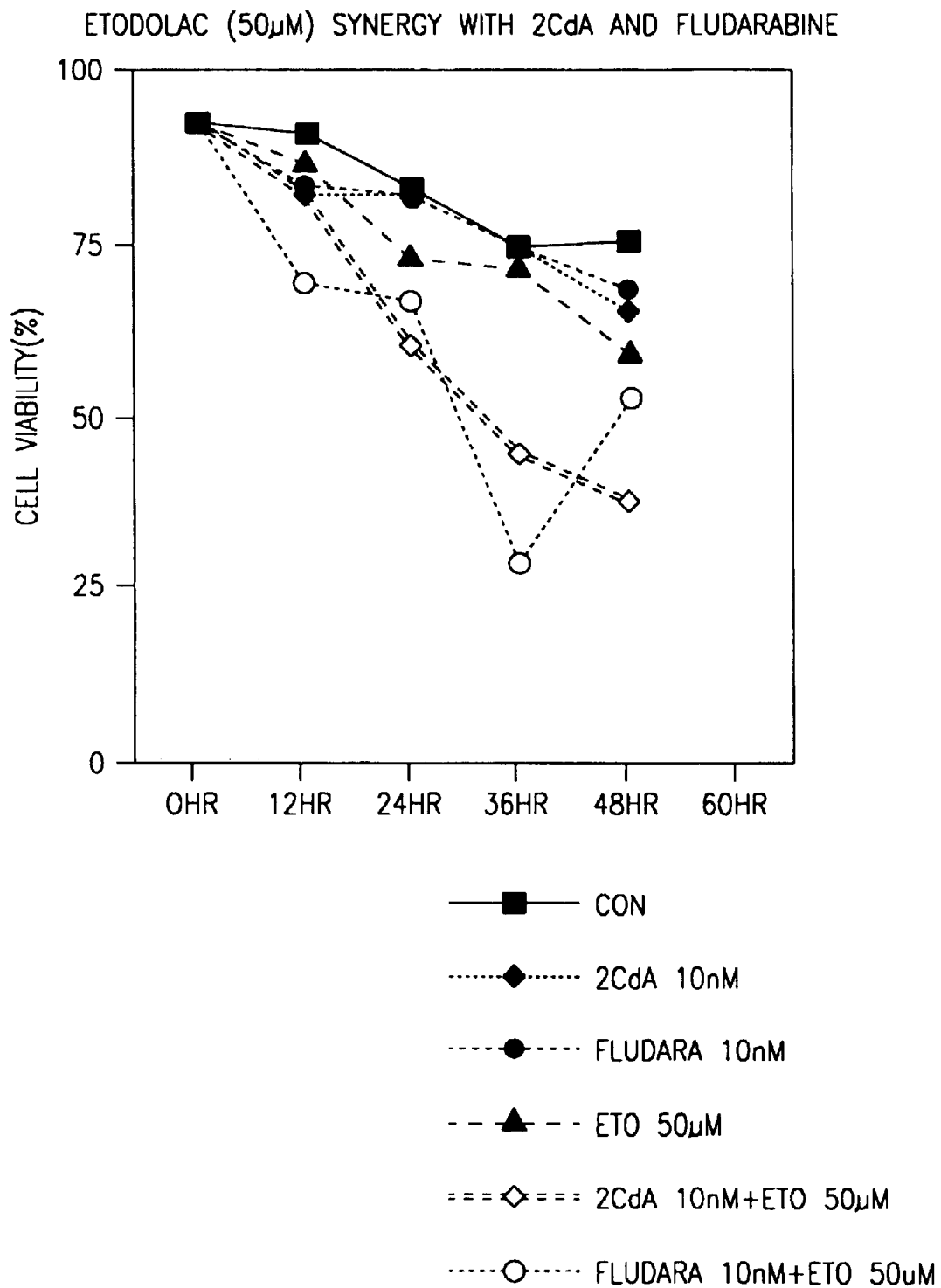
FIG. 4 is a graph depicting the synergistic effect of a combination of 50 μM etodolac with 10 μM 2 CdA or 10 mM Fludara against CLL cells.

Fludarabine is a nucleoside analog commonly used for the treatment of CLL. In this experiment the in vitro survival of CLL cells at the indicated time points was compared in cultures containing medium alone ("Con", squares), fludarabine 10 nM (diamonds), etodolac 10 μM (closed circles), and fludarabine 10 nM plus etodolac 10 μM (open circles). The two drugs together exhibited a synergistic cytotoxic effect. FIG. 3 shows that the combination killed 50% of CLL cells during 48 hours of culture, while either drug alone was ineffective. FIG. 4 demonstrates synergy between 50 μM etodolac and 10 nM 2-chlorodeoxyadenosine and fludarabine, under the same test conditions.

EXAMPLE 3

Effect of R(–) and S(+) Etodolac Against CLL Cells

Etodolac tablets were ground in a mortar and extracted from the formulation using ethyl acetate. The resulting racemic mixture of enantiomers was separated into R and S isomers on a preparative scale by fractional crystallization by the procedure of Becker-Scharfenkamp and Blaschke, *J. Chromagtog.*, 621, 199 (1993). Thus, the racemic mixture solid was dissolved in absolute 2-propanol and S-1-phenylethylamine was added to the solution. The resulting salt solution was stored in the refrigerator for 4 days. The crystalline white salt product was filtered and washed with cold 2-propanol and recrystallized two more times from 2-propanol. The same procedure was repeated for the R isomer only using R-1-phenylethylamine as the resolving agent. Finally, the R and S salts were decomposed using 10% sulfuric acid (v/v) and extracted with ethyl acetate. The chiral purity of each isomer was verified by HPLC using a Chiral-AGP column from ChromTech.

Figure 5:
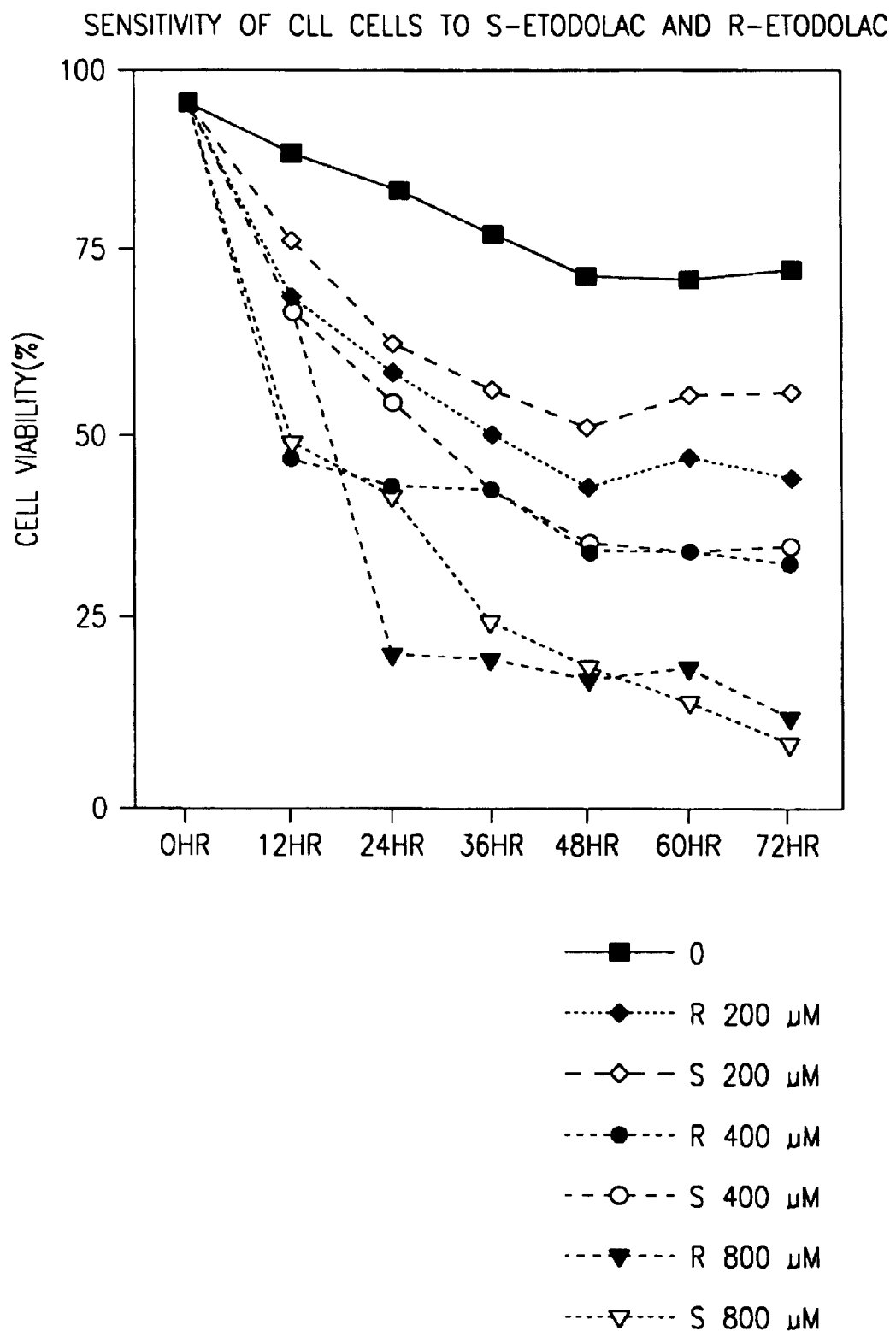
FIG. 5 is a graph depicting the sensitivity of CLL cells to S- and R-etodolac.

The toxicities of the two enantiomers to CLL cells cultured in RPMI 1640 medium with 10% autologous plasma were compared at the indicated concentrations and time points, as shown in FIG. 5. The R- and S-enantiomers are equivalently cytotoxic to the CLL cells.

EXAMPLE 4

Viability of CLL Cells Before and After Etodolac Treatment

Figure 6:
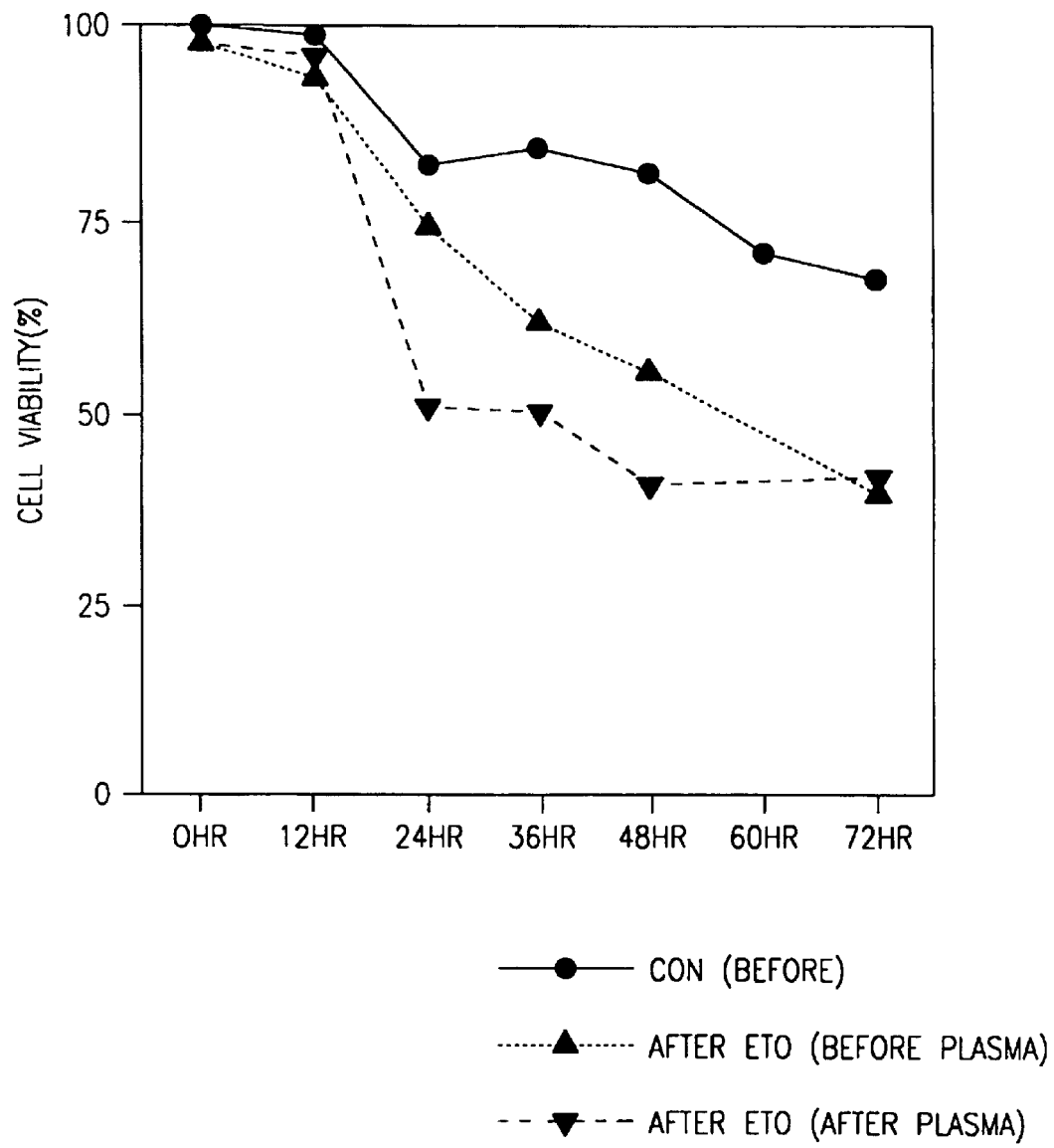
FIGS. 6 and 7 depict the viability of CLL cells from two patients before and after etodolac administration.
Figure 7:
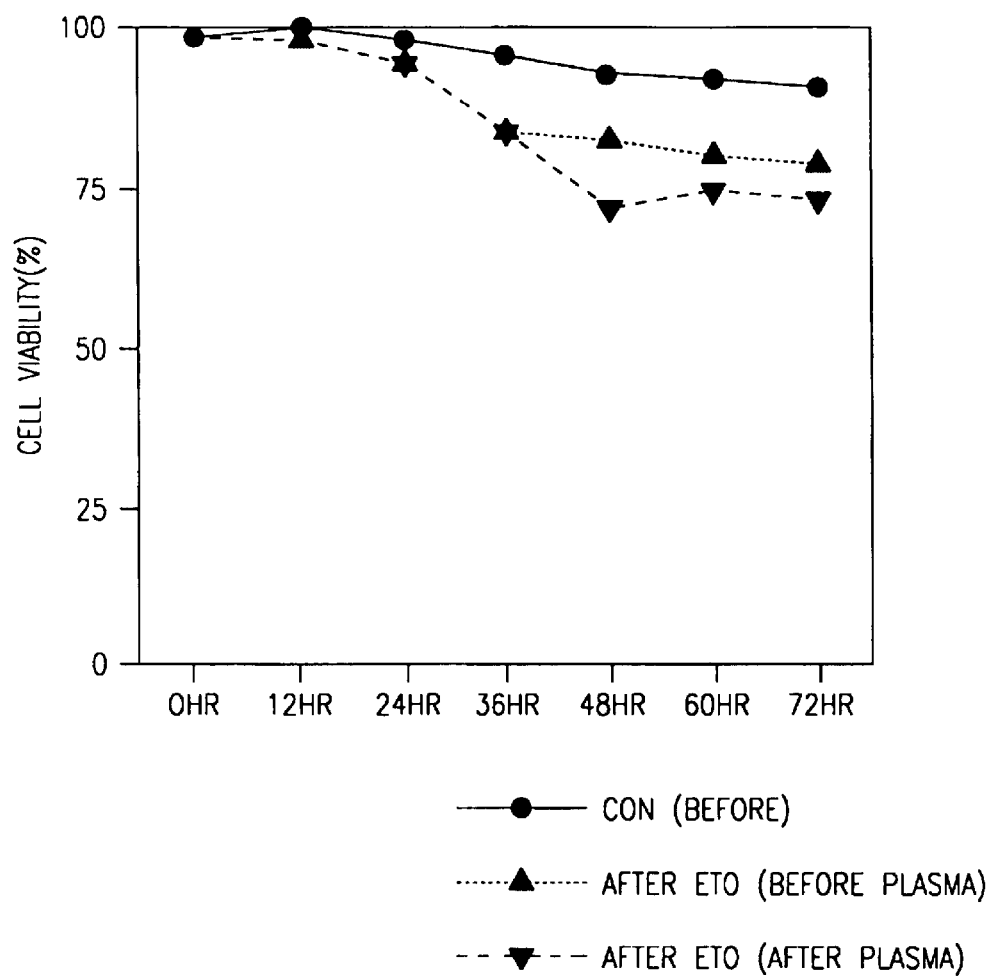
Figure 8A:
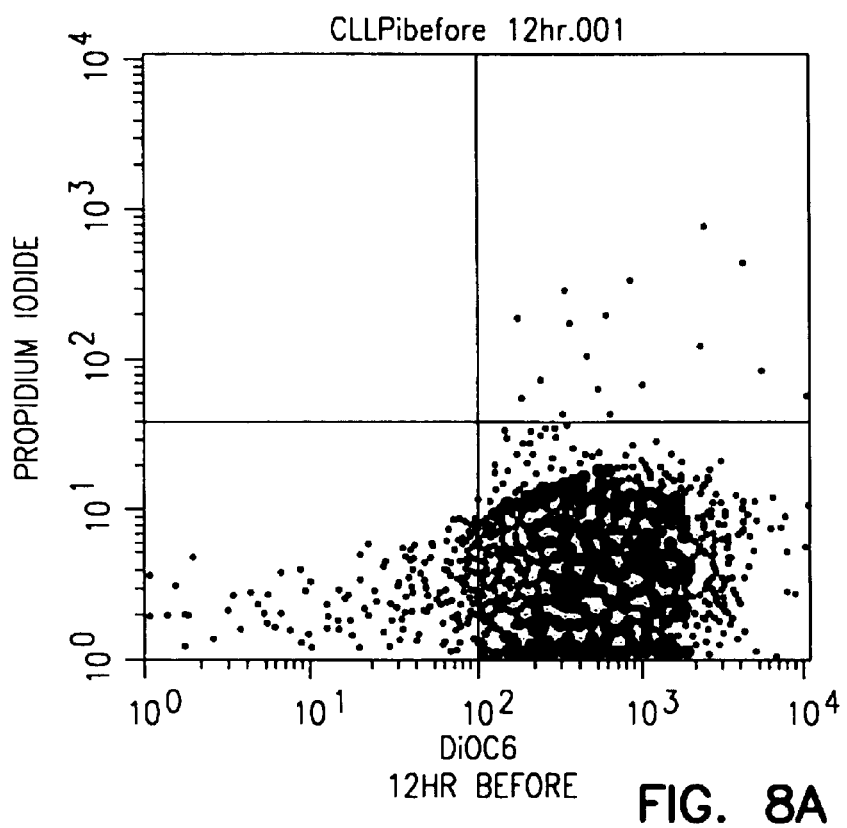
FIGS. 8A, 8B, 8C and 8D depict a flow cytometric analysis of CLL cells before and after etodolac treatment.
Figure 8B:
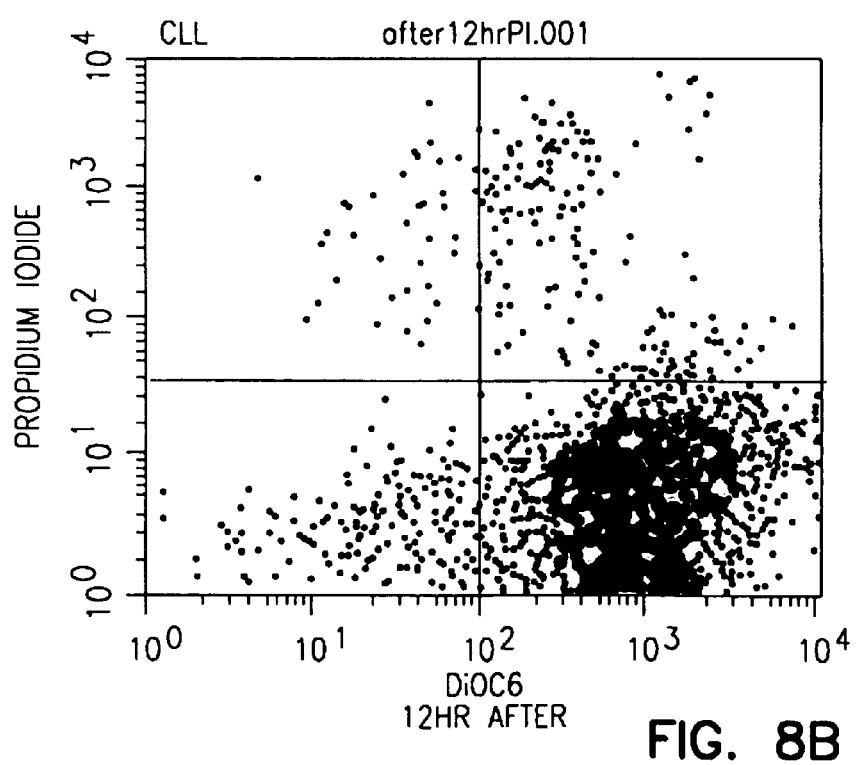
Figure 8C:
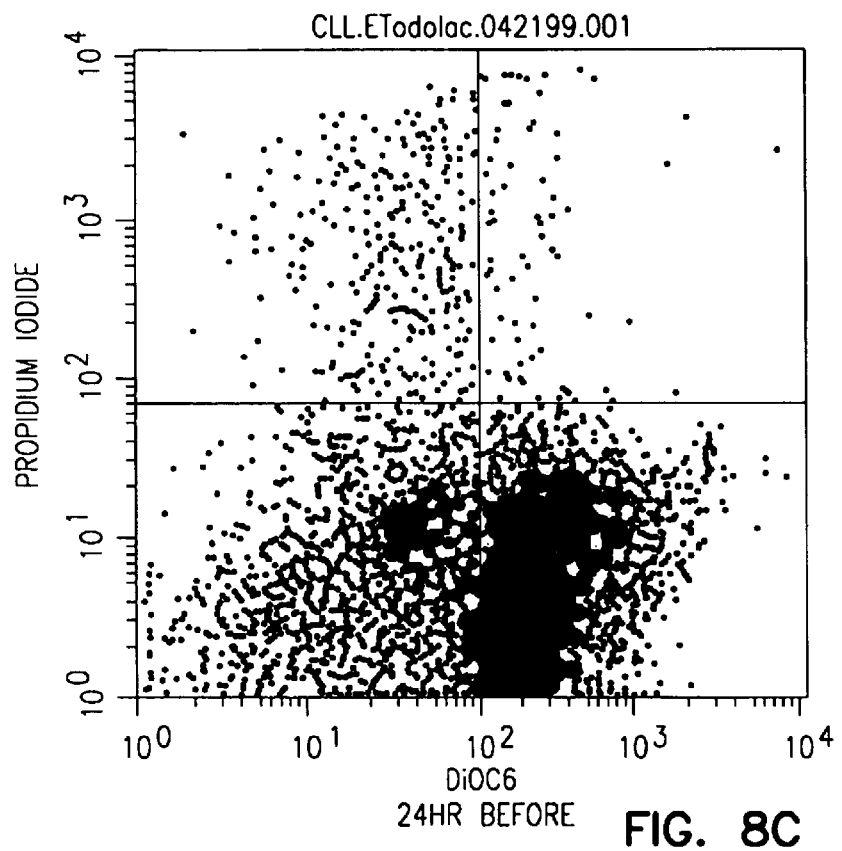
Figure 8D:
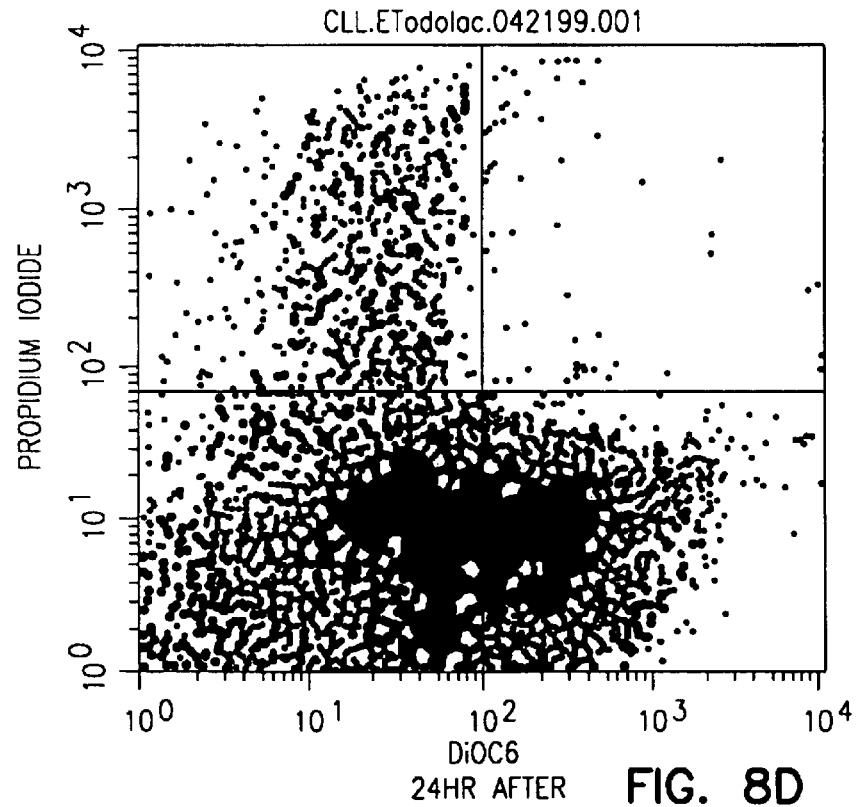

Heparinized blood was taken from two patients (JK and NA) with CLL. Then each patient immediately took a 400 mg etodolac tablet, and a second tablet 12 hours later. After another 12 hours, a second blood specimen was obtained. The CLL cells were isolated and their survival in vitro were compared in RPMI 1640 medium containing 10% autologous plasma, as described in Example 1. The circles show CLL cells before etodolac treatment. In FIGS. 6–7, the upward pointing triangles represent CLL cell viability after etodolac treatment, wherein the cells are dispersed in medium containing the pretreatment plasma. The downward pointing triangles are CLL cells after treatment maintained in medium with the post-treatment plasma.

FIG. 6 shows the different survivals of the two cell populations from patient JK. Note that the cells after treatment had a shortened survival compared to the cells before treatment. FIG. 7 shows a less dramatic but similar effect with patient NA. FIG. 8 is a flow cytometric analysis of CLL cells from patient JK before and after etodolac treatment. $DiOC_6$ is a dye that is captured by mitochondria. When cells die by apoptosis, the intensity of staining decreases. The X axis on the four panels in FIG. 8 shows the $DiOC_6$ staining. An increased number of dots in the left lower box indicates cell death by apoptosis. If one compares the cells taken from the patient before etodolac treatment, and after etodolac treatment, one can see that the number of dots in the left lower box is much higher after the drug. This effect is detectable at 12 hours, and increases further after 24 hours.

To conduct the flow cytometric analysis, the mitochondrial transmembrane potential was analyzed by 3,3' dihexyloxacarboncyanide iodide ($DiOC_6$), cell membrane permeability by propidium iodide (PI)[3] and mitochondrial respiration by dihydrorhodamine 123 (DHR) (See J. A. Royall et al., *Arch. Biochem. Biophys.*, 302, 348 (1993)). After CLL cells were cultured for 12 or 24 hours with the indicated amount of etodolac, the cells were incubated for 10 minutes at 37° C. in culture medium containing 40 nM of $DiOC_6$ and 5 µg/ml PI. Cells were also cultured for 3 hours with the indicated amount of etodolac, spun down at 200×g for 10 minutes and resuspended in fresh respiration buffer (250 mM sucrose, 1 g/L bovine serum albumin, 10 mM $MgCl_2$, 10 mM K/Hepes, 5 mM $KH_2PO_4$ (pH 7.4)) and cultured for 10 minutes at 37° C. with 0.04% digitonin. Then cells were loaded for 5 minutes with 0.1 µM dihydrorhodamine (DHR). Cells were analyzed within 30 minutes in a Becton Dickinson FAC-Scalibur cytofluorometer. After suitable comprehension, fluorescence was recorded at different wavelength: $DiOC_6$ and DHR at 525 nm (Fl-1) and PI at 600 nm (FL-3).

As a general matter a reduction of 10% in the survival of the post-treatment malignant cells, compared to the pretreatment malignant cells, at 16 hours after culture in vitro is considered a "positive" in this test, and indicates the use of etodolac, i.e., R(−) etodolac in CLL or other cancer therapy.

EXAMPLE 5

Ability of R(−)-Etodolac to Selectively Kill MM Cells

Figure 9:
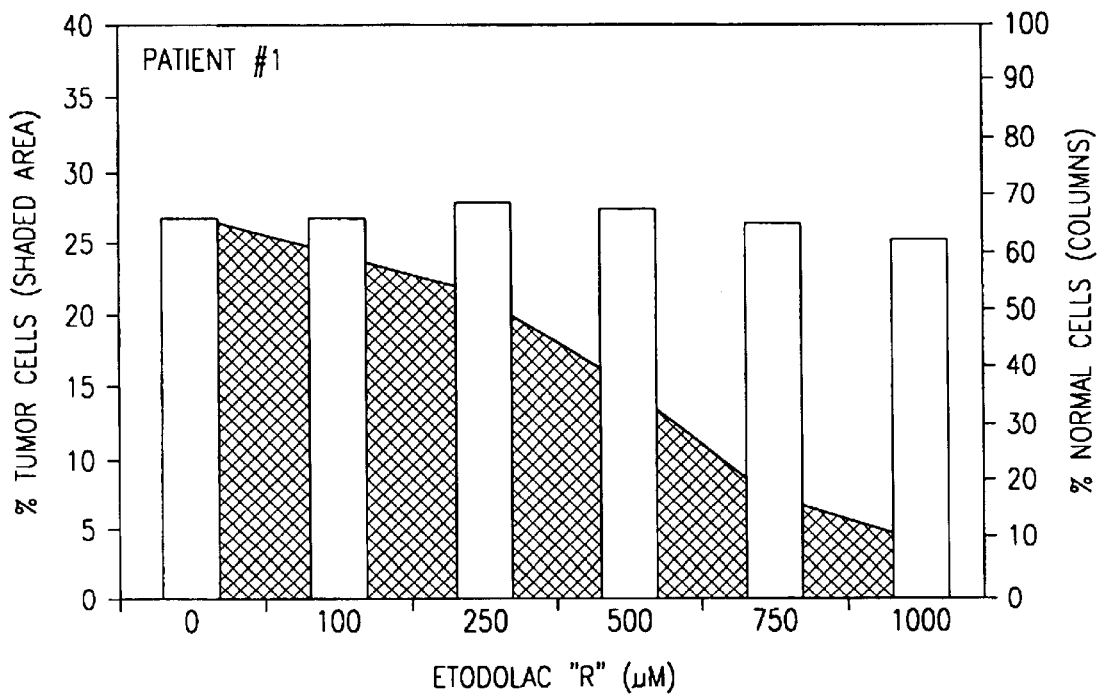
FIGS. 9 and 10 depict the selective action of R(−)-etodolac against MM cells from two patients.
Figure 10:
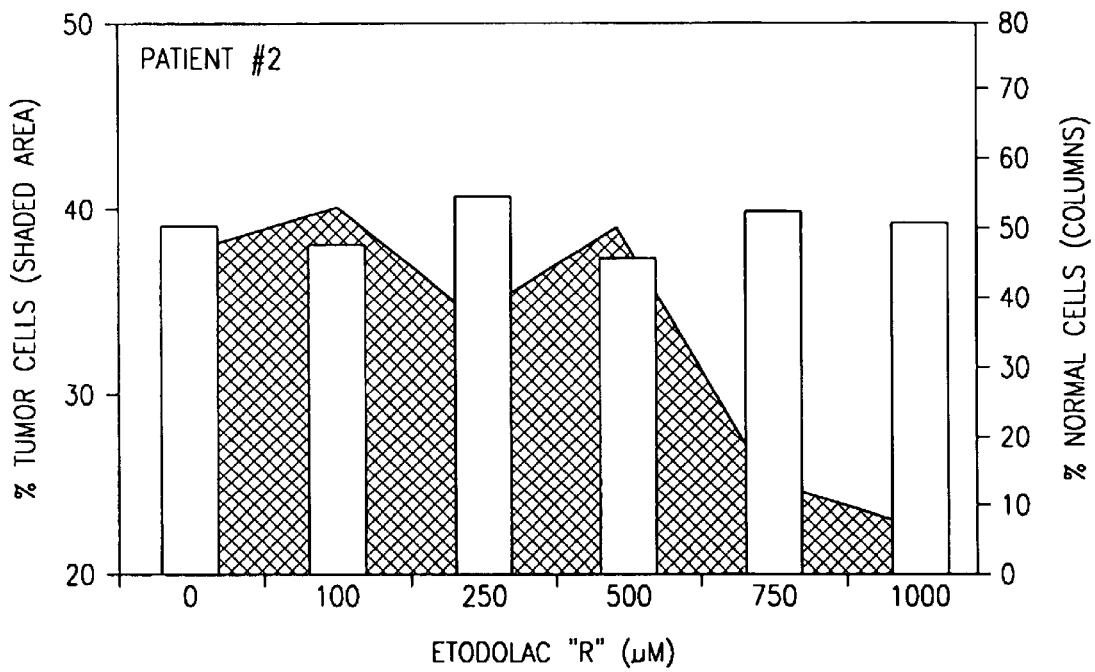

Bone marrow was obtained from two patients with multiple myeloma. The marrow contained a mixture of malignant cells, as enumerated by high level expression of the CD38 membrane antigen, and normal cells. The suspended marrow cells were incubated for 72 hours in RPMI 1640 medium with 10% fetal bovine serum, and various concentrations of the purified R-enantiomer of etodolac. Then the dead cells were stained with propidium iodide, and the multiple myeloma cells were stained with fluorescent monoclonal anti-CD38 antibodies. The data were analyzed by fluorescent activated cell sorting. FIGS. 9–10 show that R-etodolac did not kill the normal bone marrow cells (light bars), but dose-dependently killed the multiple myeloma cells (dark shaded areas), in the marrow cells from both patients.

EXAMPLE 6

Etodolac Cytotoxicity to Cancer Cell Lines

Table 1 summarizes the cytotoxic effects of R(−)-etodolac toward prostate cancer cell lines and one colon cancer cell line are indeed within clinically achievable concentrations, given that a 1 gram dosage of R(−)-etodolac should yield a maximal plasma concentration in a human subject of about 400 µM. The fact that the R(−)- and S(+)-enantiomers are both cytotoxic indicates that the anti-prostate cancer activity is COX independent. Note that R(−)-etodolac, which is devoid of anti-inflammatory activity, nonetheless is more toxic to prostate cancer cells than is S(+) etodolac.

TABLE 1

| Cell line | Origin | Etodolac R/S | Etodolac R | Etodolac S | Phenoty |
|---|---|---|---|---|---|
| PC-3 | Prostate | 340 ± 20* | 150 ± 15* | 800 + 30* | Sensitive |
| LNCaP-FGC | Prostate | 400 ± 35 | 270 ± 50 | 220 ± 20 | Sensitive |
| Alva-31 | Prostate | >1000 | >1000 | >1000 | Resistant |
| OVCAR-3 | Ovarian | >1000 | >1000 | >1000 | Resistant |
| MDA-MB-231 | Breast | >1000 | >1000 | >1000 | Resistant |
| HCT-116 | Colon | 450 ± 15 | 280 ± 20 | 420 ± 50 | Sensitive |
| SW260 | Colon | 1000 ± 120 | ND | ND | Resistant |
| A549 | Lung | >1000 | >1000 | >1000 | Resistant |

*$IC_{50}$ (µM) of Etodolac R/S, R or S. Cytotoxicity was assessed by MTT assay after three days continuous exposure to decreasing concentrations of the agent. The results were confirmed by FACS using propidium iodide uptake.

EXAMPLE 7

Etodolac Downregulation of Mcl-1 and Bag-1

Figure 11A:
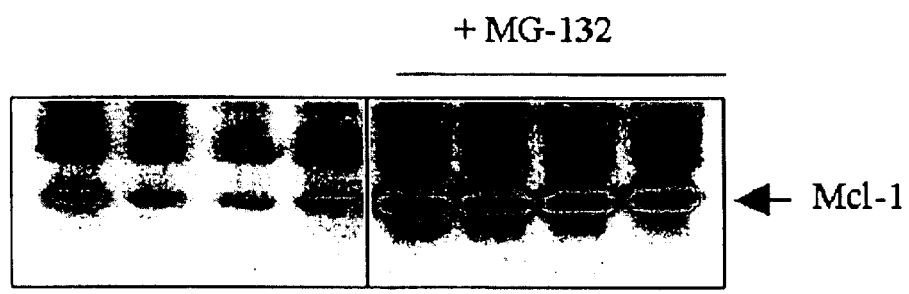
FIGS. 11A and 11B are photocopies of a SDS-PAGE gels demonstrating that etodolac induces a rapid downregulation in Mcl-1 (Panel A) and Bag-1 (Panel B), that is blocked by MG-132.
Figure 11B:
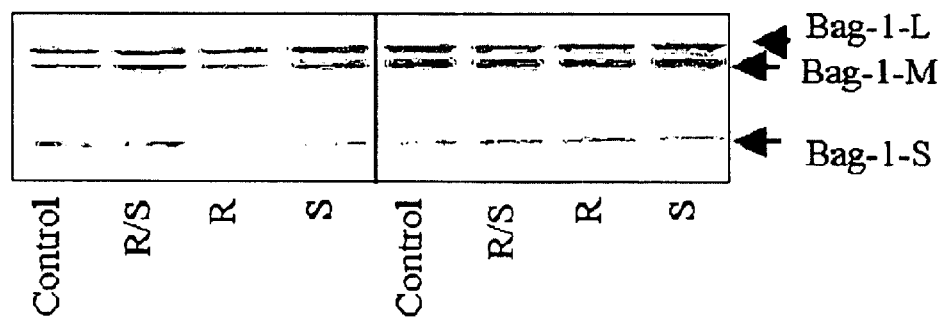

As planar hydrophobic compounds, etodolac and other NSAIDS can readily insert into cell and organ membranes, and can disrupt their structure and function (S. B. Abramson et al., *Arthritis and Rheumatism*, 32, 1 (1989)). The proteins Mcl-1 and Bag-1 are anti-apoptotic members of the bcl-2 family that are found in mitochondria (X. Wang et al., *Exp. Cell Res.*, 235, 210 (1997)). As early as two hours after incubation with 100 µM etodolac, Mcl-1 and Bag-1 levels fell in an etodolac sensitive prostate cancer cell line (LNCaP). The fall in Mcl-1 and Bag-1 levels was prevented by co-incubation of the prostate cells with 5.0 µM MG-132, a recently described inhibitor of the proteasome (FIG. 11, Panels A and B, respectively) (D. H. Lee at al., *Trends Cell Biol.*, 8, 397 (1998)). Detergent lysates (20 µg per lane) were subjected to SDS-PAGE and immunoblotted with anti-Mcl-1 and anti-Bag-1 antibodies. Pre-incubation of the cells with Z-VAD, a broad-spectrum caspase inhibitor, did not prevent the Mcl-1 and Bag-1 downregulation. Etodolac incubation did not alter Bcl-2 and Bax levels (data not shown). Thus, etodolac did not interfere with Mcl-1 synthesis, but probably accelerated its turnover. Both R- and S-etodolac induced Mcl-1 degradation at equivalent concentrations.

EXAMPLE 8

Expression of PPAR-γ in Cancer Cell Lines

Figure 12:
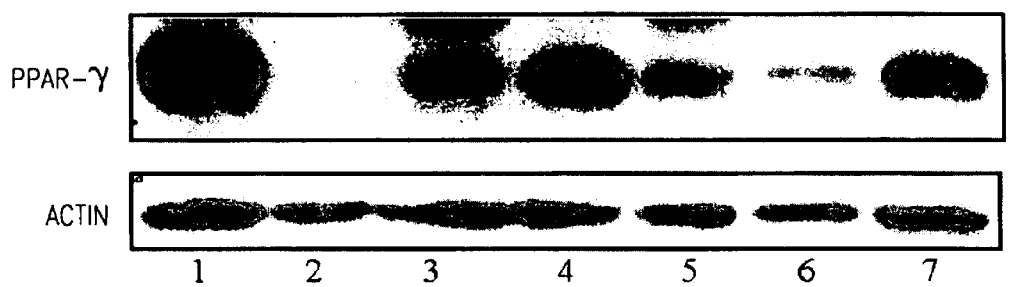
FIG. 12 is a photocopy of an SDS-PAGE gel depicting expression of PPAR-γ by seven cancer cell lines.

Although etodolac has not been previously studied, high concentrations of other NSAIDs have been reported to activate the nuclear hormone receptor PPAR-γ (J. M. Lehmann et al., *J. Biol. Chem.*, 272, 3406 (1997). Moreover, maximal activation of PPAR-γ induces apoptosis in human macrophages (G. Chinetti et al., *J. Biol. Chem.*, 273, 25579 (1998). Therefore, it was of interest to determine if prostate cells express PPAR-γ, and to compare the expression level with other cancer types. Detergent lysates (20 µg per lane) obtained from subconfluent cell lines were subjected to SDS-PAGE and immunoblotted with anti-PPAR-γ antibodies. To normalize the PPAR-γ content, the membrane was reblotted with an anti-actin monoclonal antibody. Lane 1: PC-3, Lane 2: SW260, Lane 3: A549, Lane 4: MDA-MB-231, Lane 5: Alva-31, Lane 6: LNCaP, Lane 7: HCT-116 (see Table 1). It was observed that some etodolac-susceptible prostate cells (PC3 especially) expressed remarkably high levels of immunoreactive PPAR-γ (FIG. 12).

EXAMPLE 9

Activation of PPAR-γ by Etodolac

Figure 13:
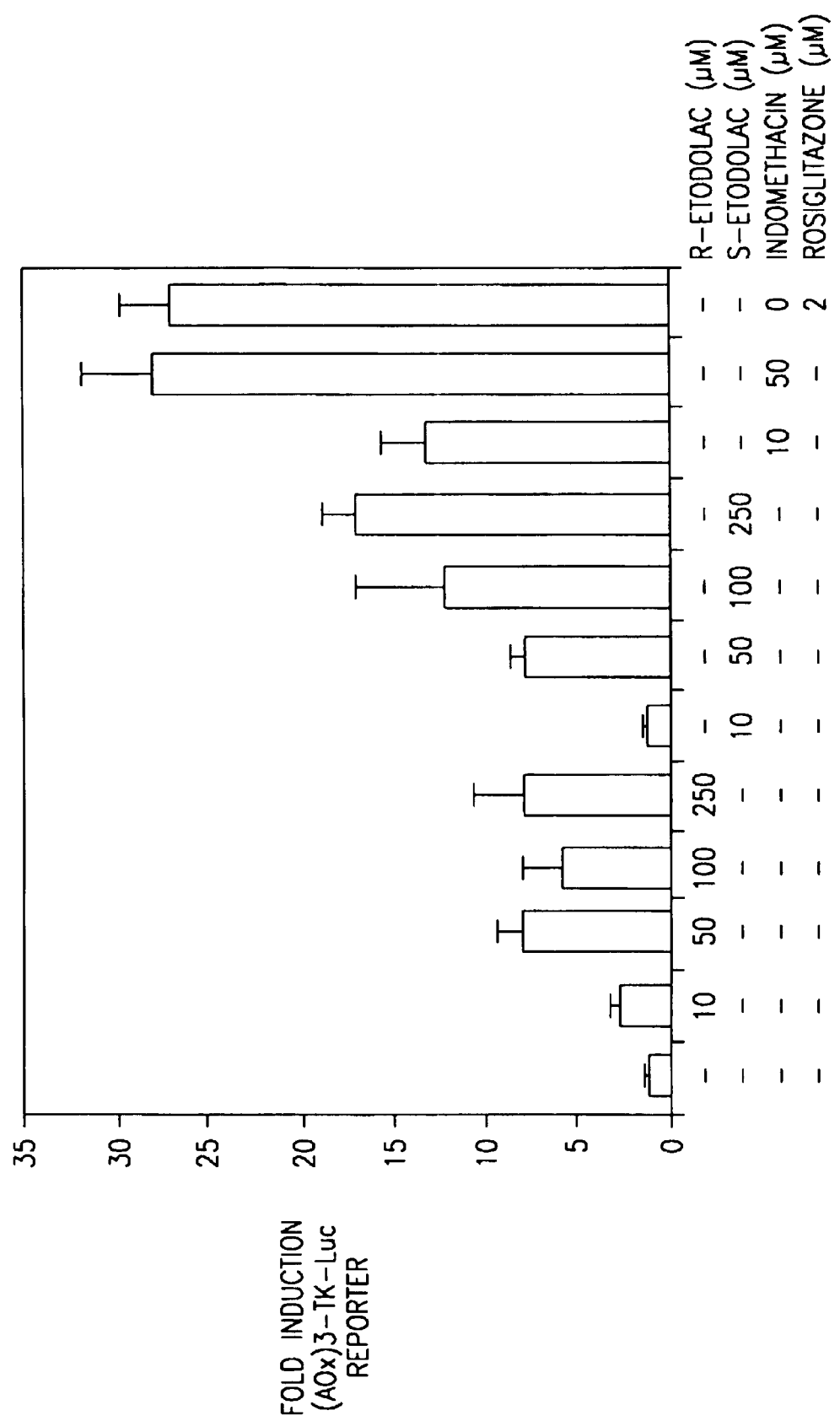
FIG. 13 is a graph depicting induction of PPAR-γ expression by etodolac and indomethacin.
Figure 14:
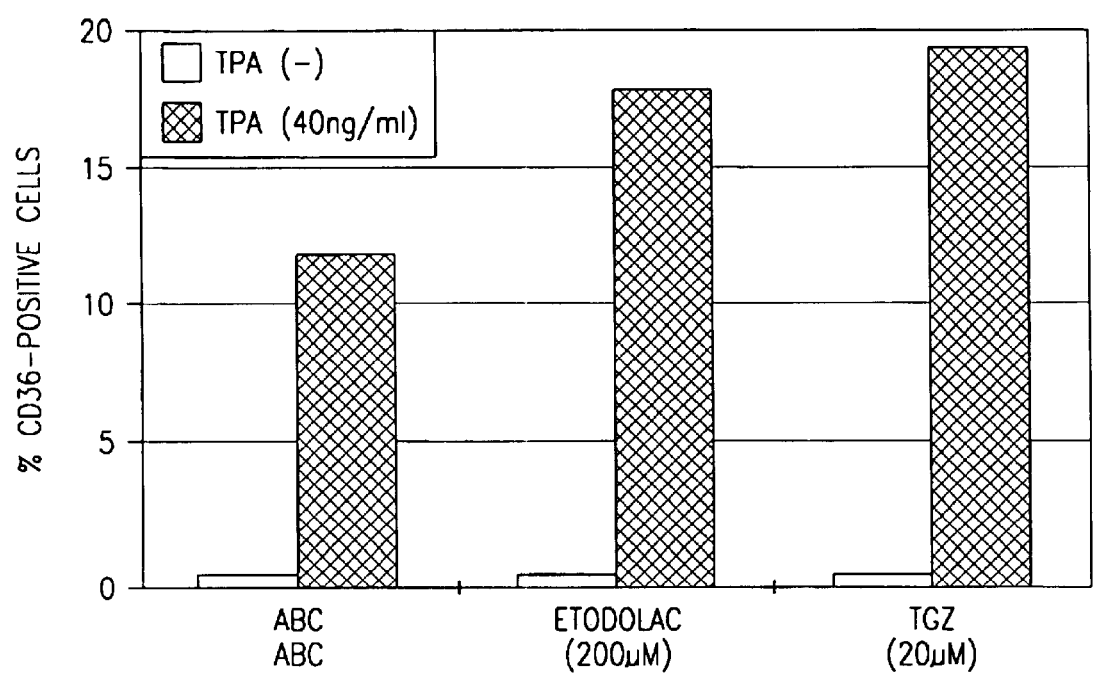
FIG. 14 is a graph depicting expression of CD36 induced by etodolac and TGZ, in the presence and absence of TPA in human monocytes.

RAW264.7 cells were transfected at a density of 3×10⁵ cells/ml in six well plates using lipofectamine with the PPAR-γ expression vector pCMX-PPAR-γ (0.1 µg), and the PPAR-γ reporter construct (AOx)₃-TK-Luc (1 µg) as previously described by M. Ricote et al., *Nature*, 391, 79 (1998). Cells were treated for 24 hours with the compounds indicated on FIG. 13, harvested and assayed for luciferase activity. Results are expressed as the mean±SD. As shown in FIG. 13, both the R- and S-enantiomers of etodolac activated a PPAR-γ reporter gene construct at concentrations readily achieved in human plasma after in vivo administration. THP-1 human monocytic cells (ATCC) were incubated in the presence or absence of phorbol ester (40 ng TPA) and 200 µM racemic etodolac or 20 µM troglitazone. After three days of culture, the surface expression of the scavenger receptor CD36 was measured by flow cytometry. As shown in FIG. 14, both R- and S-etodolac caused the expression of CD36, a marker of PPAR-γ activation, in the human cell line THP-1 during macrophage differentiation.

EXAMPLE 10

Etodolac Treatment of Prostate Cancer Tissue Samples

Figure 15:
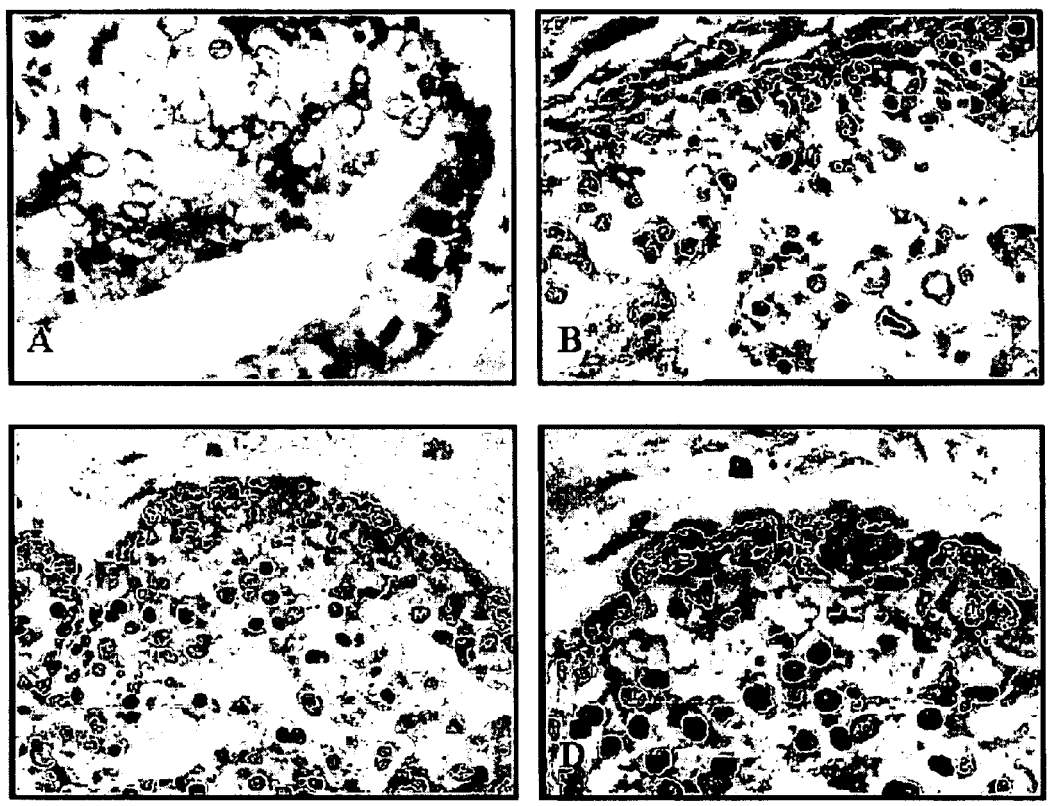
FIGS. 15A, 15B, 15C and 15D are photographs of sections of prostate cancer tissue, untreated (A) or treated (B, C, D) with etodolac.

Freshly obtained prostatectomy samples were cut into 3 mm³ pieces, and incubated for 72 hours in RPMI-1640 supplemented with 10% FBS and antibiotics in the absence (A, 400×) or presence of racemic etodolac (B, 400×) or the purified R enantiomer (C, 400×; and D, 630×). The tissues were next fixed in 4% paraformaldehyde in PBS, embedded in paraffin, sectioned and stained with hematoxylin and eosin. FIG. 15A shows the infiltrating tumor cells (large nuclei) and some residuel normal epithelium. FIGS. 15 B to 15 D show the effect of etodolac: note the abundant presence of pyknotic apoptotic nuclei (dark arrows, B and D), and the disintegration of the neoplastic glandular architecture (B+C). Etodolac was found to be selectively toxic to the tumor cells, but did not affect normal basal cells. The racemic mixture (R/S) and the purified R and S analogs were found both active.

EXAMPLE 11

Prospective Protocol for Screening to Identify Etodolac Analogs

A. Screening of analogs by competition against radiolabeled R-etodolac

Etodolac-sensitive chronic lymphocytic leukemia [CLL] cells, or other cancer cells, will be utilized for drug screening in radioreceptor binding assay. In brief, frozen CLL cells will be washed three times in Hanks' Balanced Salt Solution (HBSS) and resuspended in HBSS-HEPES. The assay will be done in a total volume of 200 µl containing approximately 2 million cells, [3H]-R-Etodolac [sp.act.20–25 Ci/mmol, prepared by Sibtech] and potential competitors or buffer are incubated in at varying temperatures [4 and 37° C.] and times [0–60 minutes]. For each sample, triplicate 50 µl aliquots will be layered over 300 µl 20% sucrose in HBSS-HEPES in 1.5 ml polypropylene snap top tubes and pelleted for 2.5 minutes at 15000 rpm in a Beckman microfuge. This procedure rapidly separates the cell-bound and cell-free etodolac. The tube tips will be cut off and the cell pellets will be solubilized and counted in a scintillation counter. Some of the incubation mixtures will contain excess unlabeled etodolac as a control. Specific binding is the difference in the bound cpm in tubes containing the radiolabeled etodolac minus the cpm in the tubes containing the radiolabeled etodolac and the excess cold competitor etodolac. Test agents are compared to the unlabeled cold competitor etodolac for their abilities to inhibit radiolbeled etodolac binding. Compounds that can inhibit the binding of radiolabeled etodolac to its receptor(s) are advanced to the next screen.

B. Intracellular $Ca^{2+}$ mobilization in CLL

Increase of intracellular calcium levels in CLL cells by test compounds such as etodolac analogs will be measured by a flow cytometric assay (FACS) and by using a fluorometric imaging plate reader syste (FLIPR, Molecular Devices Corp., Sunnyvale, Calif.) using the Fluo-4 dye (Molecular Probes). Briefly, CLL cells (5×10⁶/ml) will be loaded for 30 min with 4 µM of Fluo-4 at 37° C. in serum-free medium, washed twice, and resuspended for an additional 30 min in normal cell culture medium. The loaded cells will be then mixed in FACS tubes with medium containing a test agent, and immediately thereafter the fluorescence will be followed by FACS analysis over a period of 3 minutes. For high-throughput screening (HTS) assays, the FLIPR-based assay will allow screening in a 96-well plate format, using the same fluorometric dye (Fluo-4). Positive controls will be performed using the calcium ionophore ionomycin at 50 mg/ml final concentration, with chemokines such as SDF-1 and IP-10, and with anti-IgM cross-linking antibodies. Compounds that increase the $Ca^{+2}$ uptake by CLL cells, preferably to at least the level induced by R(-)-etodolac are advanced to the next screen.

C. Chemotaxis and chemokinesis assays

Cell migration will be measured in a 24-well modified Boyden chamber (Transwell, Corning-Costar, NY). The recombinant human IP-10 chemokine (R&D Systems, McKinley Place, Nebr.) will be diluted in RPMI-1640 medium at 200 ng/ml, and used to evaluate the chemotactic properties of lymphocytes from B-CLL patients. Polycarbonate membranes with pore size of 3 mm will be used. A total of 600 mL of chemokines or control medium will be added to the bottom wells, and 100 mL of 2 to 5.0×106 cells/ml cells resuspended in RPMI-1640 will be added to the top wells. The chamber will be incubated at 37° C. with 5% $CO_2$ for 2 hours. The membranes will then be removed, and the cells present on the bottom well will be quantified by flow cytometry. For cell quantification, a fixed acquisition time of 30 seconds will be used per sample, and beads will be run during each experiment to ensure a reproducible acquisition. Test agents that induce a chemokinetic response in the lymphocytes, such a chemotactic response, preferably at least as effectively as R(−) etodolac, will be advanced to the next screen.

D. Induction of apoptosis in cancer cells

The pro-apoptotic activity of the test agents, e.g., the R-etodolac analogs, will be tested in primary CLL cells, as well as in other tumor cells, by using the MTT assay and by measuring the catalytic activation of caspase-3 using a fluorometric assay. In brief, cells will be incubated for up to 3 days in presence of serial dilutions of the selected test agents. Cells viability will be quantified in 96-well plates by adding the MTT reagent (at 1 mg/ml final) for 2–4 hours followed by SDS cell lysis and spectrophotometric analysis at 570 nm. Caspase catalytic activity will be measured in a 96-well plate assay using a specific fluorometric substrate (DEVD-AMC), after lysing the treated cells with a CHAPS/NP-40 lysing buffer followed by fluorometric analysis. Test agents that exhibit pro-apoptotic activity, e.g., that increase caspase activity, preferably at least as effectively as R(−)-etodolac, will be advanced to the next screen.

E. Lymphocyte depletion in mouse

The selected test agent will be orally delivered to mice of various backgrounds in a single dose of 25 and 100 mg/kg. The number of white blood cells will be counted using a neubauer chamber after 4, 24 hrs, 7 and 14 days post treatment. Test agents that do not lower white cell levels substantially, preferably no more than does R(−) etodolac, will be advanced to the next screen.

F. Tumor animal model

The anti-cancer and preventive activity of the R-etodolac analogs will be tested using the pristane-induced mouse myeloma model, and the transgenic adenocarcinoma mouse prostate (TRAMP) model. The mice will receive a diet supplemented with 0.05% to 0.5% of the selected test agent or control. The experimental diets will be in the form of sterile pellets containing the test agent (provided by Dyets Inc., Pa.). For prevention of cancer experiments in the mouse myeloma model, the diet will be initiated at the same time as the first pristane injection. For the transgenic prostate cancer model, the diet will begin at birth. For therapeutic experiments, the diet will begin in the TRAMP mice at week 10, when the first histological pathologic markers are usually observed. Analogs will advance to clinical trials or further development based on their activity to inhibit cancer in at least one of these screens.

All of the publications and patent documents cited hereinabove are incorporated by reference herein. The invention has been described with reference to various specific and preferred embodiments and techniques. However, it should be understood that many variations and modifications may be made while remaining within the spirit and scope of the invention.

What is claimed is:

1. A method of treating leukemia, multiple myeloma or prostate cancer in a mammal comprising administering an effective amount of a compound of formula (I):

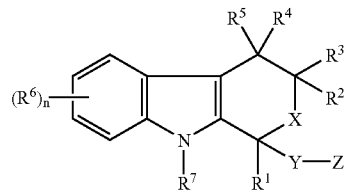

wherein $R^1$ is lower alkyl, lower alkenyl, (hydroxy)lower alkyl, lower alkynyl, phenyl, benzyl or 2-thienyl, $R^2$, $R^3$, $R^4$ and $R^5$ are the same or different and are each hydrogen or lower alkyl;

each $R^6$ is individually hydrogen, lower alkyl, hydroxy, (hydroxy)lower alkyl, lower alkoxy, benzyloxy, lower alkanoyloxy, nitro or halo, n is 1–3, $R^7$ is hydrogen, lower alkyl or lower alkenyl, X is oxy or thio, Y is carbonyl, $(CH_2)_{1-3}$, $(CH_2)_{1-3}SO_2$ or $(CH_2)_{1-3}C(O)$, and Z is (ω-(4-pyridyl)($C_2$–$C_4$alkoxy), (ω-(($R^8$)($R^9$) amino) ($C_2$–$C_4$ alkoxy), wherein $R^8$ and $R^9$ are each H, ($C_1$–$C_3$)alkyl or, together with N, are a 5- or 6-membered heterocyclic ring having 1–3 N($R^8$), S or nonperoxide O; an amino acid ester of (ω-(HO)($C_2$–$C_4$))alkoxy, N($R^8$)CH($R^8$)$CO_2$H, 1'-D-glucuronyloxy, OH, ($C_2$–$C_4$)acyloxy, $SO_3H$, $PO_4H_2$, N(NO)(OH), $SO_2NH_2$, PO(OH)($NH_2$), $OCH_2CH_2N(CH_3)_3{}^+$, amino, lower alkylamino, di(lower alkyl)amino, phenylamino, or tetrazolyl;

or a pharmaceutically acceptable salt thereof; to a mammal afflicted with leukemia, multiple myeloma or prostate cancer.

2. The method of claim 1 wherein the treatment is for prostate cancer.

3. The method of claim 1 wherein the treatment is for multiple myeloma.

4. The method of claim 1 wherein the leukemia is chronic lymphocytic leukemia.

5. The method of claim 1 wherein the compound of formula I is administered orally.

6. The method of claim 5 wherein an enterically coated dosage form is administered.

7. The method of claim 1 wherein the compound of formula (I) is administered parenterally.

8. The method of claim 1 wherein the compound of formula (I) is administered in combination with a chemotherapeutic agent.

9. The method of claim 2 wherein the compound of formula (I) is administered in combination with a chemotherapeutic agent.

10. The method of claim 8 wherein the chemotherapeutic agent is mitoxantrone, prednisone, estramustine, melphalan, vinblastine or a combination thereof.

11. The method of claim 9 wherein the chemotherapeutic agent is an anti-androgen.

12. The method of claim 11 wherein the anti-androgen is bicafutamide, nilutamide, flutamide, cycloproterone acetate or a combination thereof.

13. The method of claim 11 wherein the anti-androgen is leuprolide acetate, goserelin acetate or a combination thereof.

* * * * *

UNITED STATES PATENT AND TRADEMARK OFFICE
CERTIFICATE OF CORRECTION

| | | |
|---|---|---|
| PATENT NO. | : 7,151,100 B1 | Page 1 of 3 |
| APPLICATION NO. | : 09/634207 | |
| DATED | : December 19, 2006 | |
| INVENTOR(S) | : Carson et al. | |

It is certified that error appears in the above-identified patent and that said Letters Patent is hereby corrected as shown below:

On the title page, in item (63), under "Related U.S. Application Data", in column 1, line 2, after "1999" insert -- , now Pat. No. 6,545,034 --.

On the title page, in item (56), under "Foreign Patent Documents", in column 1, line 13, delete "WO-02/021225" and insert -- WO-02/02125 --, therefor.

On page 2, in item (56), under "U.S. Patent Documents", in column 1, line 32, below "5,824,699" insert -- 5,939,455 8/1999 Rephaeli 514/547 --.

On page 2, in item (56), under "U.S. Patent Documents", in column 1, line 43, below "2002/0042375" insert -- 2003/0004142 1/2003 Prior et al. 514/165 --.

On page 2, in item (56), under "Other Publications", in column 2, lines 38–41, delete ""Treatment of Prostate Cancer: Watchful Waiting, Radical Prostatectomy, and Cryoablation", Seminars in Surgical Oncology, 18(1), pp. 37-44, Jan./Feb. 2000)" and insert -- "Enhancement of Chemotherapeutic Drug Toxicity to Human Tumour Cells In Vitro by a Subset of Non-Steroidal Anti-Inflammatory Drugs (NSAIDs)", European Journal of Cancer, 34 (8), pp. 1250-1259, (Jul. 1998). --, therefor.

On page 2, in item (56), under "Other Publications", in column 2, line 61, below "1997)." insert -- Leman, Eddy S., et al., "Characterization of the Nuclear Matrix Proteins in a Transgenic Mouse Model for Prostate Cancer", Journal of Cellular Biochemistry, 86, (2002), 203–212.--.

On page 3, in item (56), under "Other Publications", in column 2, line 7, delete "Etodalac" and insert -- Etodolac --, therefor.

On page 3, in item (56), under "Other Publications", in column 2, line 33, delete "Ademomas" and insert -- Adenomas --, therefor.

On page 3, in item (56), under "Other Publications", in column 2, line 37, delete "Flubiprofen" and insert -- Flurbiprofen --, therefor.

On page 3, in item (56), under "Other Publications", in column 2, line 38, delete "Enatiomer" and insert -- Enantiomer --, therefor.

On Sheet 4 of 15, in FIG. 4, line 7 (Excluding Graph), delete "50uM" and insert -- $50\mu M$ --, therefor.

In column 1, line 7, after "1999," insert -- now U.S. Patent No. 6,545,034, --.

UNITED STATES PATENT AND TRADEMARK OFFICE
CERTIFICATE OF CORRECTION

PATENT NO. : 7,151,100 B1
APPLICATION NO. : 09/634207
DATED : December 19, 2006
INVENTOR(S) : Carson et al.

It is certified that error appears in the above-identified patent and that said Letters Patent is hereby corrected as shown below:

In column 2, lines 60–61, delete "1'-D-glucuronyloxy," and insert -- $OCH_2CH_2N(CH_3)^+_3$, or 1'-D-glucuronyloxy; or Y-Z is $(CH_2)_{1-3}R^{10}$ wherein $R^{10}$ is --, therefor.

In column 2, line 62, after "$PO(OH)NH_2$," delete "$OCH_2CH_2N(CH_3)^+_3$".

In column 2, line 65, delete "calls" and insert -- cells --, therefor.

In column 3, line 9, delete "chromic" and insert -- chronic --, therefor.

In column 3, line 33, delete "chlorodenosine" and insert -- chloroadenosine --, therefor.

In column 3, line 34, delete "chemoterapeutic" and insert -- chemotherapeutic --, therefor.

In column 3, line 64, after "cancer" insert -- cell --.

In column 5, line 45, delete "or" and insert -- $OCH_2CH_2N(CH_3)^+_3$, --, therefor.

In column 5, line 46, after "alkylamino," insert -- [(carboxy)(lower alkyl)] --.

In column 5, line 47, after "phenylamino," insert -- or Y-Z is $(CH_2)_{1-3}R^{10}$ wherein $R^{10}$ is --.

In column 5, line 48, after "$OCH_2CH_2N(CH_3)^+_3$" insert -- , --.

In column 6, line 27, delete "metabolutes" and insert -- metabolites --, therefor.

In column 7, line 48, delete "to" and insert -- of --, therefor.

In column 8, line 47, delete "othewise" and insert -- otherwise --, therefor.

In column 9, line 38, after "the" insert -- preferred methods of preparation are vacuum drying and the freeze drying --.

In column 10, line 3, delete "Lympocytes" and insert -- Lymphocytes --, therefor.

In column 10, line 59, delete "Chromagtog" and insert -- Chromatog --, therefor.

In column 14, line 4, delete "residuel" and insert -- residual --, therefor.

UNITED STATES PATENT AND TRADEMARK OFFICE
CERTIFICATE OF CORRECTION

PATENT NO. : 7,151,100 B1
APPLICATION NO. : 09/634207
DATED : December 19, 2006
INVENTOR(S) : Carson et al.

It is certified that error appears in the above-identified patent and that said Letters Patent is hereby corrected as shown below:

In column 14, line 40, delete "radiolbeled" and insert -- radiolabeled --, therefor.

In column 14, line 47, delete "syste" and insert -- system --, therefor.

In column 14, line 60, delete "mg" and insert -- ng --, therefor.

In column 16, lines 27-34, in Claim 1, delete "wherein $R^8$ and $R^9$ are each H, $(C_1-C_3)$alkyl or, together with N, are a 5- or 6-membered heterocyclic ring having 1-3 $N(R^8)$, S or nonperoxide O; an amino acid ester of $(\omega\text{-}(HO)(C_2\text{-}C_4))$ alkoxy, N $(R^8)$ CH $(R^8)$ $CO_2H$, 1'-D-glucuronyloxy, OH, $(C_2\text{-}C_4)$acyloxy, $SO_3H$, $PO_4H_2$, N(NO)(OH), $SO_2NH_2$, PO(OH)($NH_2$), $OCH_2CH_2N(CH_3)^+_3$, amino, lower alkylamino, di(lower alkyl) amino, phenylamino," and insert -- an amino acid ester of $(\omega\text{-}(HO)(C_2\text{-}C_4))$alkoxy, $N(R^8)CH(R^8)CO_2H$, 1'-D-glucuronyloxy, or $OCH_2CH_2N(CH_3)^+_3$; wherein $R^8$ and $R^9$ are each H, $(C_1-C_3)$alkyl or together with N, are a 5- or 6-membered heterocyclic ring having 1-3 $N(R^8)$, S or nonperoxide O; or Y-Z is $(CH_2)_{1-3}R^{10}$ wherein $R^{10}$ is OH, $(C_2\text{-}C_4)$acyloxy, $SO_3H$, $PO_4H_2$, N(NO)(OH), $SO_2NH_2$, PO(OH)$NH_2$, --, therefor.

Signed and Sealed this

Twenty-fourth Day of July, 2007

JON W. DUDAS
*Director of the United States Patent and Trademark Office*